(12) United States Patent
Birikh et al.

(10) Patent No.: US 10,626,553 B2
(45) Date of Patent: Apr. 21, 2020

(54) METHOD FOR LIGNIN DEPOLYMERISATION

(71) Applicant: METGEN OY, Kaarina (FI)

(72) Inventors: Klara Birikh, Kaarina (FI); Anu Minna Maaret Suonpää, Kaarina (FI)

(73) Assignee: Metgen OY, Kaarina (FI)

( * ) Notice: Subject to any disclaimer, the term of this patent is extended or adjusted under 35 U.S.C. 154(b) by 0 days.

(21) Appl. No.: 16/320,005

(22) PCT Filed: Jul. 21, 2017

(86) PCT No.: PCT/EP2017/068436
§ 371 (c)(1),
(2) Date: Jan. 23, 2019

(87) PCT Pub. No.: WO2018/019707
PCT Pub. Date: Feb. 1, 2018

(65) Prior Publication Data
US 2019/0271112 A1    Sep. 5, 2019

(30) Foreign Application Priority Data
Jul. 25, 2016  (EP) .................................... 16181065

(51) Int. Cl.
| | | |
|---|---|---|
| *D21C 5/00* | (2006.01) | |
| *C12P 7/22* | (2006.01) | |
| *D21C 9/14* | (2006.01) | |
| *D21C 9/153* | (2006.01) | |
| *D21C 9/147* | (2006.01) | |
| *D21C 9/16* | (2006.01) | |
| *C08L 97/00* | (2006.01) | |
| *D21C 11/00* | (2006.01) | |
| *D21C 9/00* | (2006.01) | |
| *C08H 7/00* | (2011.01) | |

(52) U.S. Cl.
CPC .............. *D21C 5/005* (2013.01); *C08H 6/00* (2013.01); *C08L 97/005* (2013.01); *C12P 7/22* (2013.01); *D21C 9/00* (2013.01); *D21C 9/14* (2013.01); *D21C 9/147* (2013.01); *D21C 9/153* (2013.01); *D21C 9/163* (2013.01); *D21C 11/0007* (2013.01)

(58) Field of Classification Search
None
See application file for complete search history.

(56) References Cited

FOREIGN PATENT DOCUMENTS

| WO | 2008027501 A2 | 3/2008 |
|---|---|---|
| WO | 2013038062 A1 | 3/2013 |
| WO | 2015144679 A1 | 10/2015 |
| WO | WO 2017/102542 | * 6/2017 |

OTHER PUBLICATIONS

Preiss et al., "Alkaliphilic bacteria with impact on industrial applications, concepts of early life forms, and bioenergetics of ATP synthesis", Front. Bioeng. Biotechnol., Jun. 3, 2015, vol. 3, Article 75, pp. 1-16. doi.org/10.3389/fbioe.2015.00075.*
Bjarnestad, S & Dahlman, O., "Chemical Compositions of Hardwood and Softwood Pulps Employing Photoacoustic Fourier Transform Infrared Spectroscopy in Combination with Partial Least-Squares Analysis", Anal. Chem. 2002, 74, 5851-5858.*
PCT International Search Report and Written Opinion, Application No. PCT/EP2017/068436, dated Sep. 14, 2017, 9 pages.
Yuki et al., Draft Genome Sequences of Three Alkaliphilic Bacillus Strains, Bacillus wakoensis JCM 9140T, Bacillus akibai JCM 9157T, and Bacillus hemicellulosilyticus JCM 9152T, Genome Announcements, vol. 2, No. 1, Jan. 30, 2014 (Jan. 30, 2014), pp. e01258-13, XP055332389 DOI: 10.1128/genomeA.01258-13. The entire document.

* cited by examiner

*Primary Examiner* — Suzanne M Noakes
(74) *Attorney, Agent, or Firm* — Patent Law Works LLP

(57) ABSTRACT

The present invention is in the field of delignifying and/or bleaching of pulp, more in particular wood pulp. Such a process is useful in paper production. More in particular, the method relates to the use of an enzyme for delignification and/or bleaching, more in particular a bacterial laccase. Even more in particular, it provides a method for delignifying and/or bleaching of a pulp, comprising an enzymatic treatment step wherein lignin-containing pulp and a laccase are reacted at alkaline pH, wherein the laccase has an amino acid sequence according to SEQ ID NO: 1 or an amino acid sequence at least 90% identical to SEQ ID NO: 1.

Figure 1A:
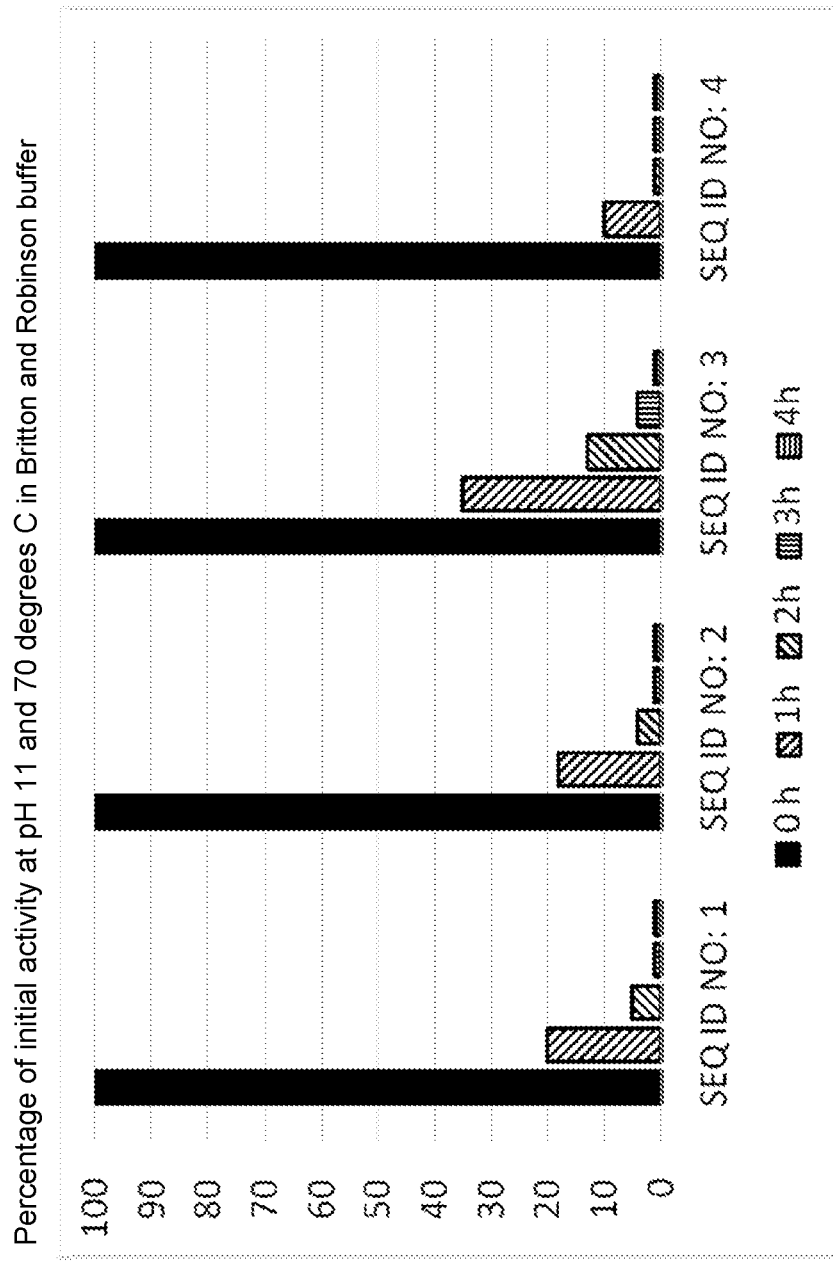

16 Claims, 14 Drawing Sheets
Specification includes a Sequence Listing.

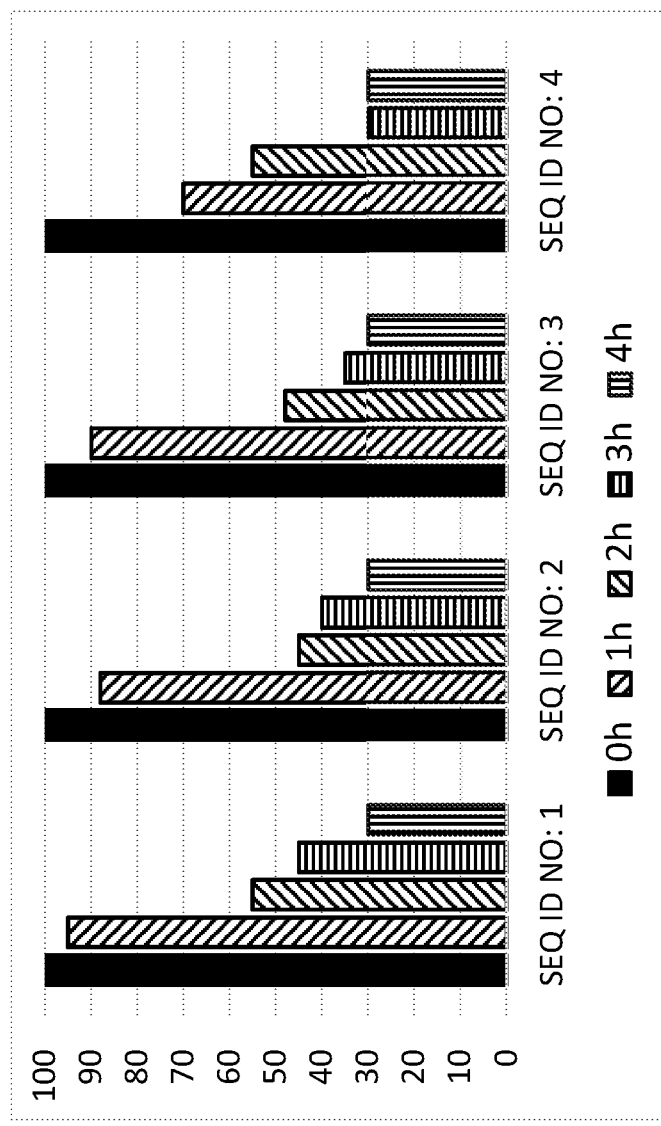
Figure 1B - Percentage of initial activity at pH 9 and 70 degrees C in Britton and Robinson buffer

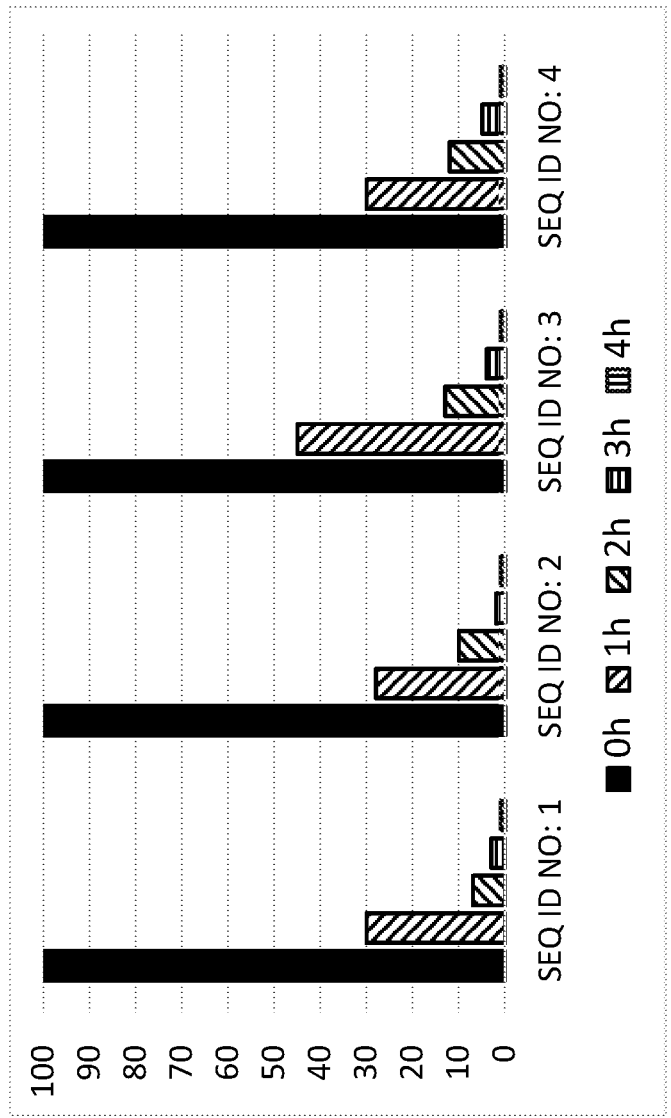
Figure 1C - Percentage of initial activity at pH 11 and 40 degrees C in Britton and Robinson buffer

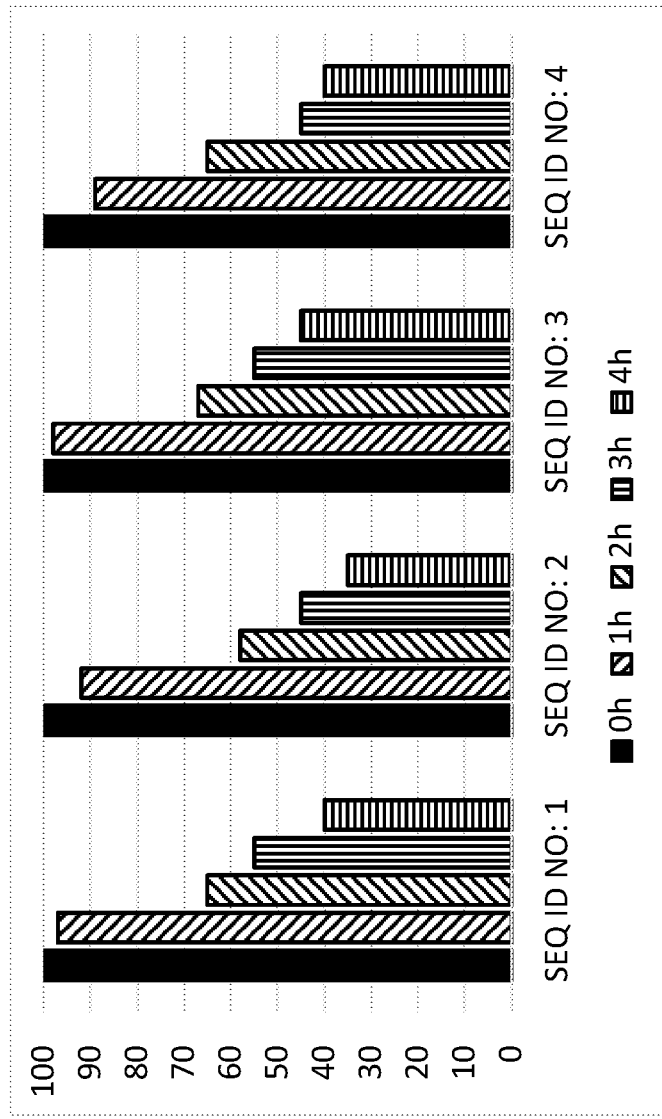

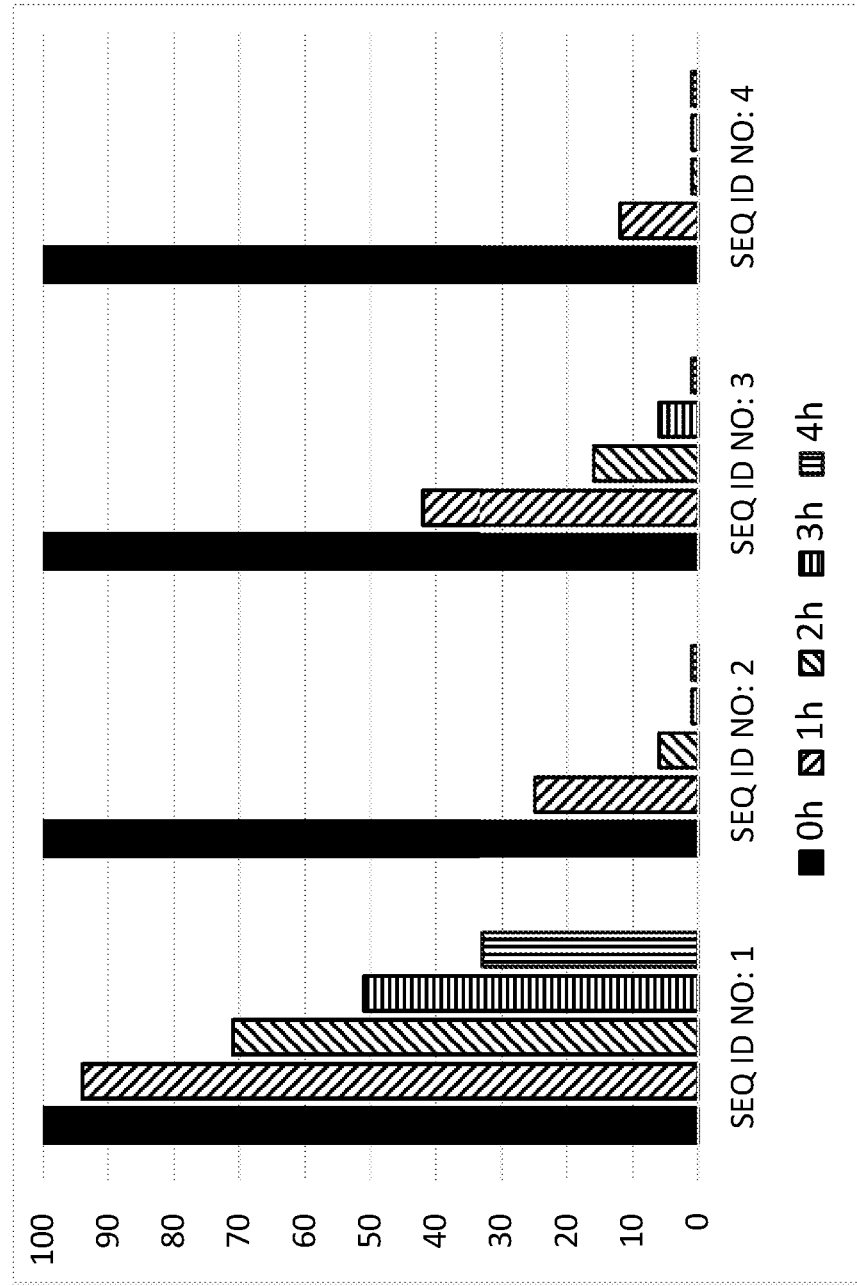

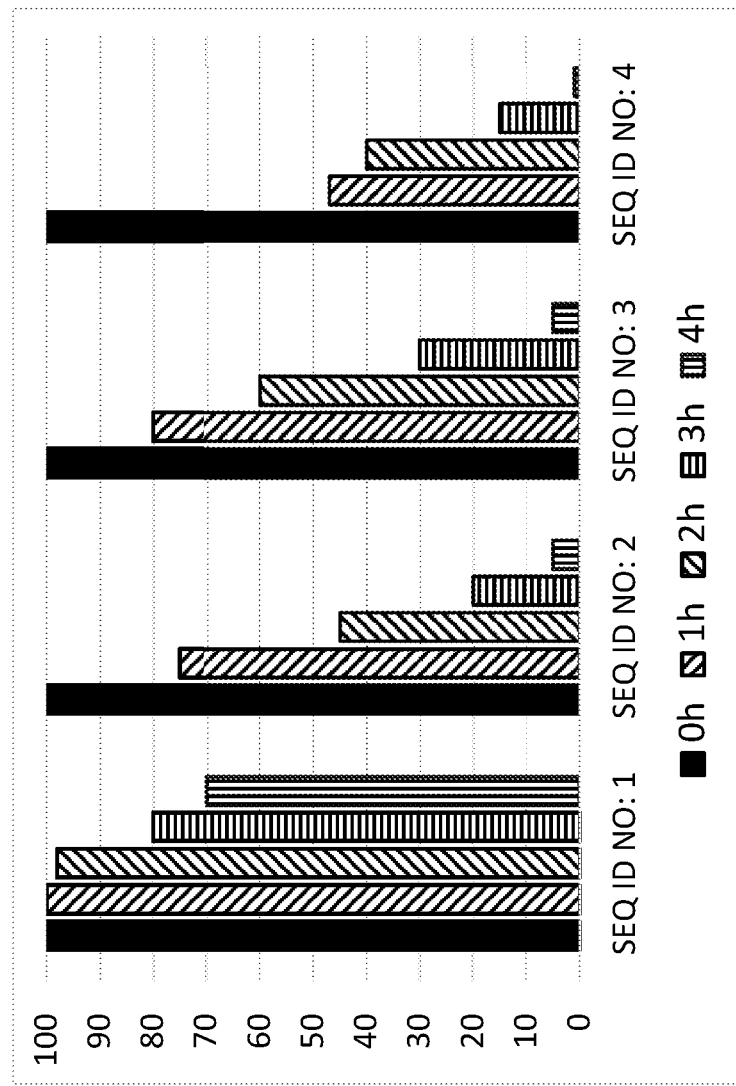
Figure 3B - Percentage of initial activity at pH 9 and 70 degrees Celsius in pulp

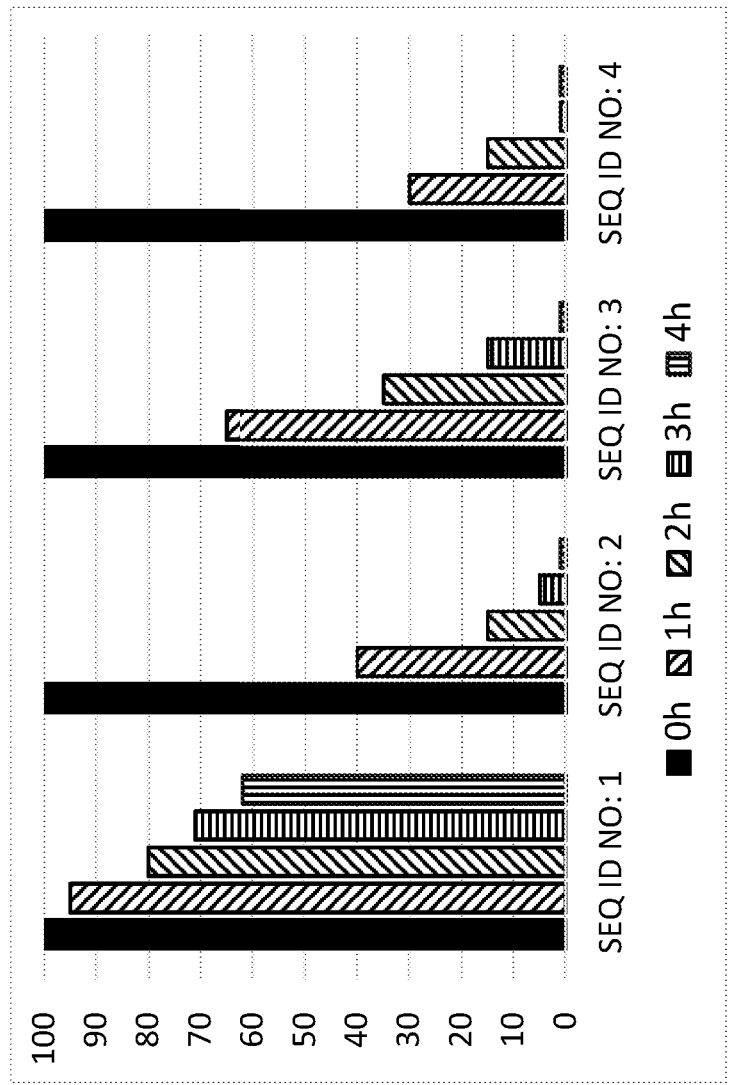
Figure 3C - Percentage of initial activity at pH 11 and 40 degrees Celsius in pulp

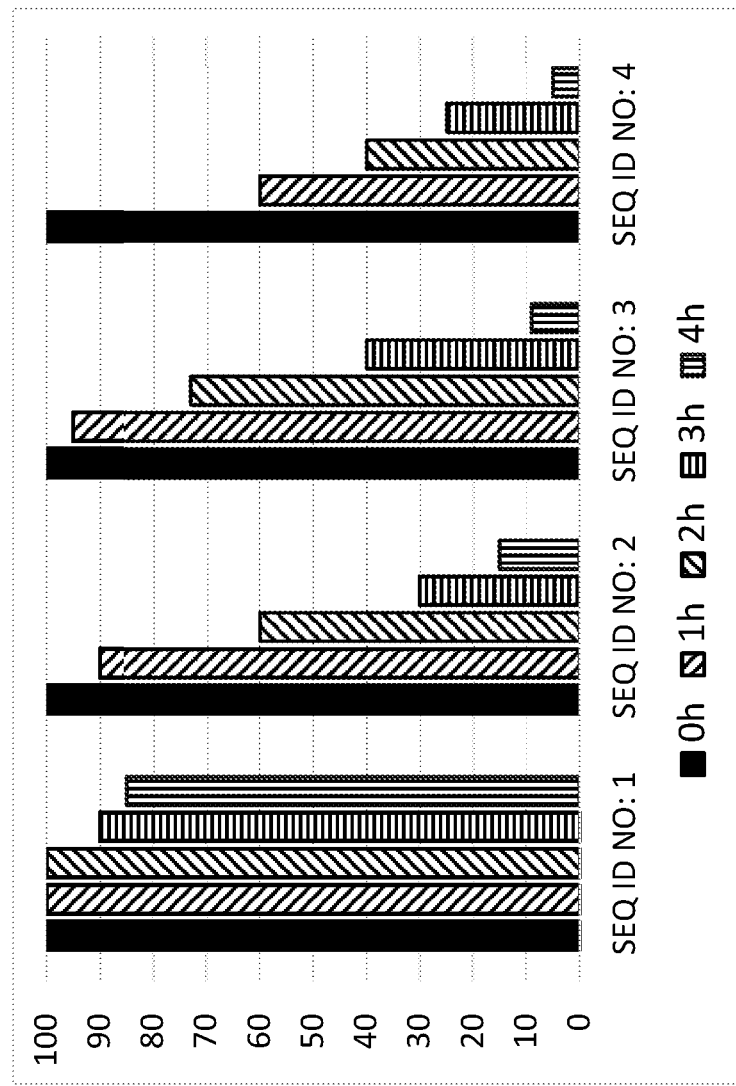
Figure 3D - Percentage of initial activity at pH 9 and 40 degrees Celsius in pulp

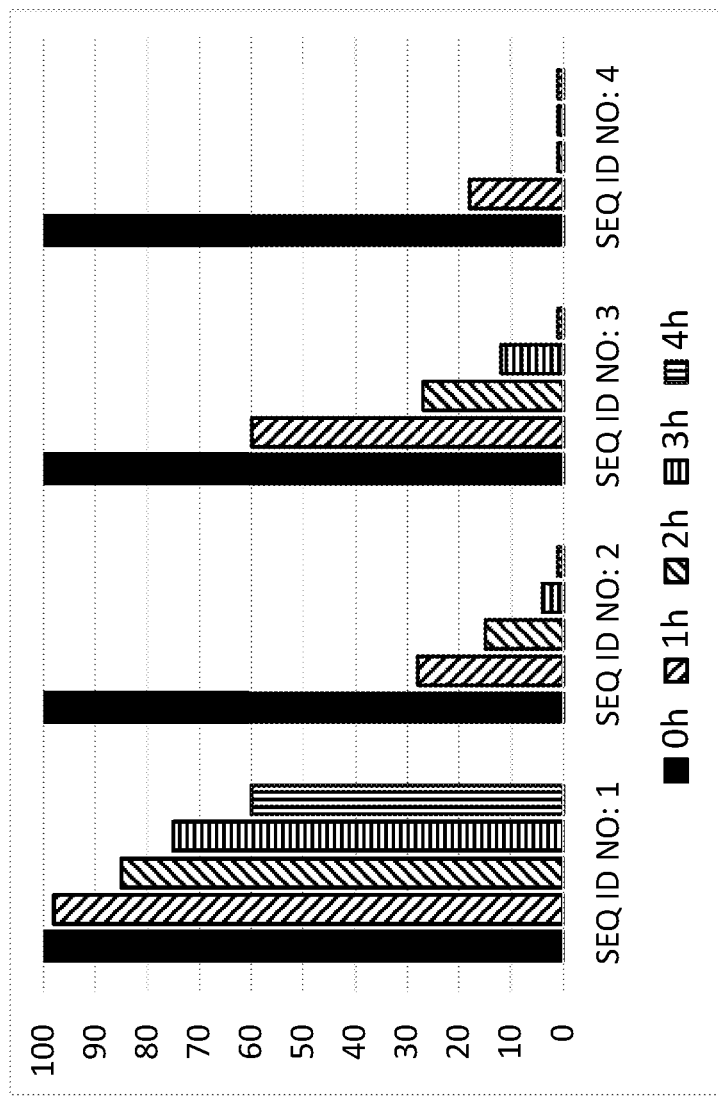
Figure 4A - Percentage of initial activity at pH 11 and 70 degrees Celsius in purified lignin

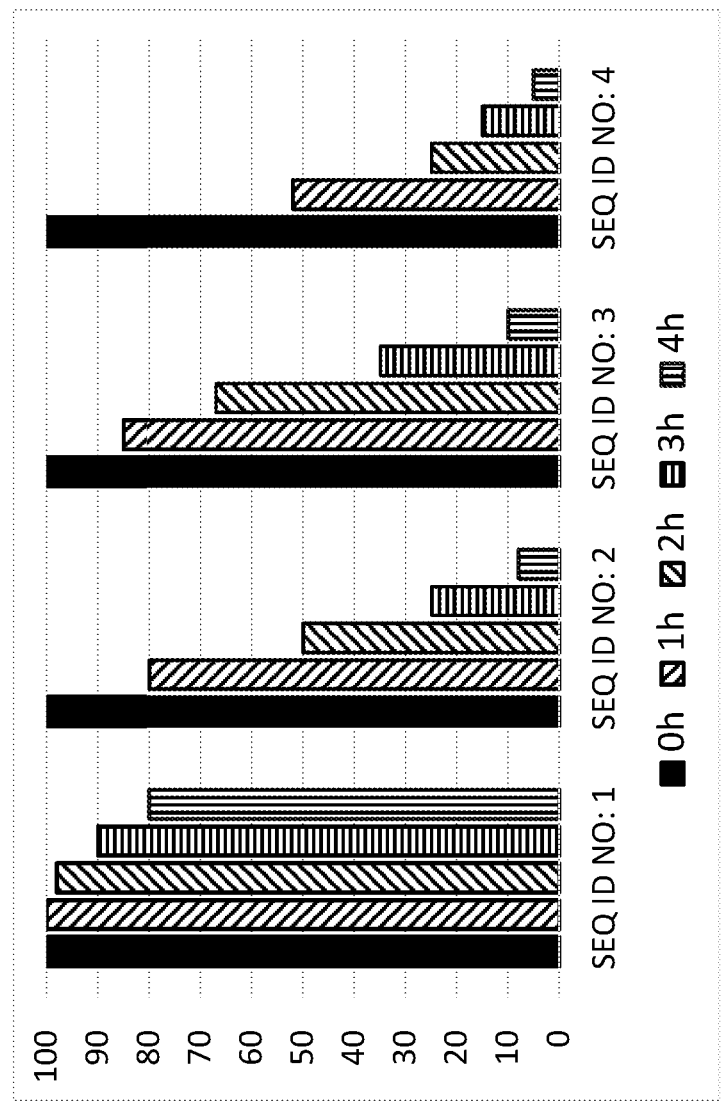
Figure 4B - Percentage of initial activity at pH 9 and 70 degrees Celsius in purified lignin

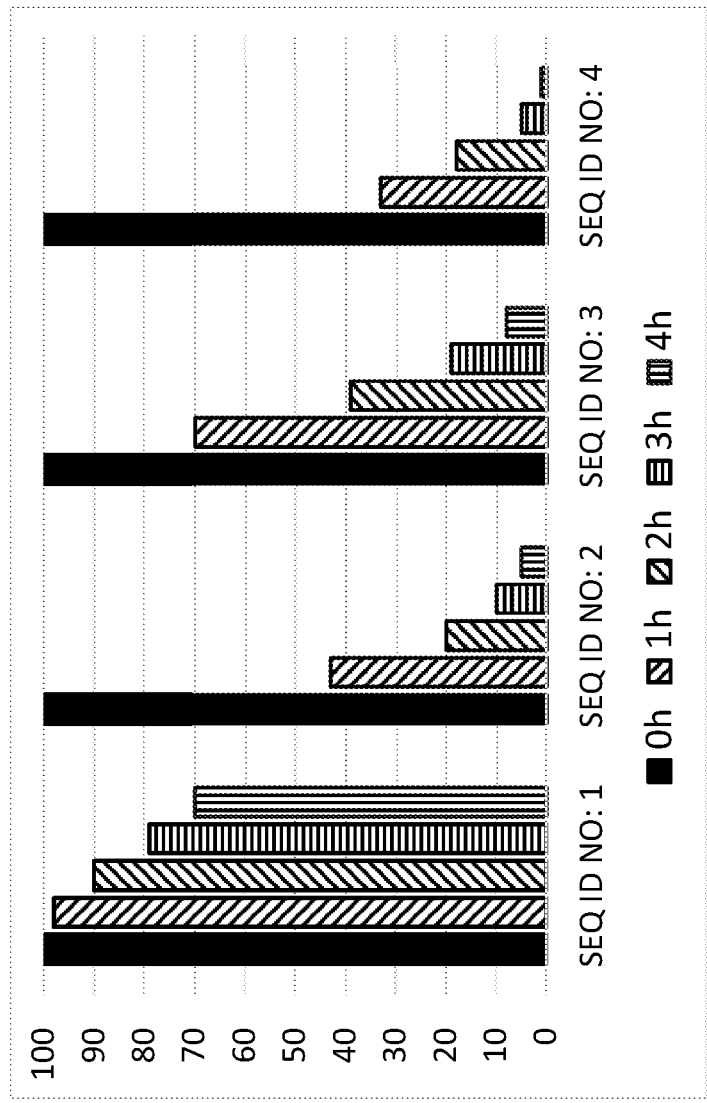
Figure 4C - Percentage of initial activity at pH 11 and 40 degrees Celsius in purified lignin

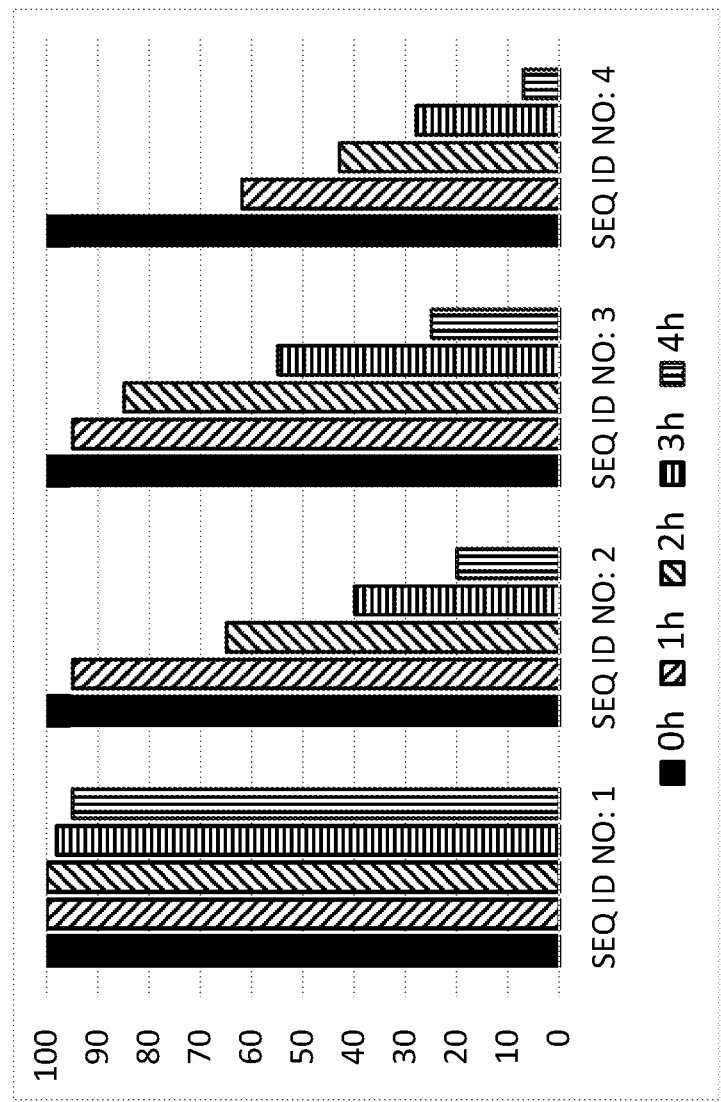
Figure 4D - Percentage of initial activity at pH 9 and 40 degrees Celsius in purified lignin

SEQUENCE LISTING

```
<160> NUMBER OF SEQ ID NOS: 8

<210> SEQ ID NO 1
<211> LENGTH: 512
<212> TYPE: PRT
<213> ORGANISM: Bacillus wakoensis

<400> SEQUENCE: 1

Met Arg Arg Lys Leu Glu Lys Phe Val Asp Ser Leu Pro Ile Met Glu
1               5                   10                  15

Thr Leu Gln Pro Lys Thr Lys Gly Lys Asn Tyr Tyr Glu Val Lys Ile
            20                  25                  30

Gln Glu Phe Lys Lys Lys Leu His Arg Asp Leu Pro Pro Thr Thr Leu
        35                  40                  45

Trp Gly Tyr Asn Ala Gln Phe Pro Gly Pro Thr Ile Glu Ala Asn Ser
    50                  55                  60

Asn Glu Pro Val Glu Val Lys Trp Ile Asn Glu Leu Pro Asn Lys His
65                  70                  75                  80

Phe Leu Pro Val Asp Trp Ser Ile Met Asn Lys Asp Leu Pro Glu Val
                85                  90                  95

Arg His Val Thr His Leu His Gly Gly Arg Thr Pro Trp Val Ser Asp
            100                 105                 110

Gly Tyr Pro Glu Ala Trp Tyr Thr Lys Asp Tyr Lys Glu Val Gly Ser
        115                 120                 125

Phe Phe Lys Glu Glu Val Tyr Arg Tyr Leu Asn Glu Gln Arg Ala Met
    130                 135                 140

Met Leu Trp Tyr His Asp His Thr Met Gly Ile Thr Arg Leu Asn Asn
145                 150                 155                 160

Tyr Ala Gly Leu Ala Gly Ala Tyr Ile Ile Arg Asp Lys His Glu Lys
                165                 170                 175

Ser Leu Asn Leu Pro Glu Gly Glu Tyr Glu Val Pro Leu Ile Ile Gln
            180                 185                 190

Asp Arg Thr Phe Asn Glu Asp Gly Ser Leu Phe Tyr Pro Thr Gly Pro
        195                 200                 205
```

Glu Asp Gly Gly Glu Asp Leu Pro Asn Pro Ser Ile Val Pro Ala Phe
210                 215                 220

Leu Gly Asp Thr Val Leu Val Asn Gly Lys Val Trp Pro Tyr Leu Glu
225                 230                 235                 240

Val Glu Pro Arg Lys Tyr Arg Phe Arg Ile Leu Asn Gly Ser Asn Thr
            245                 250                 255

Arg Ser Tyr Gln Leu His Leu Asp Ser Asn Gln Glu Val Tyr Gln Ile
            260                 265                 270

Gly Ser Asp Gly Gly Leu Leu Glu Lys Pro Val Gln Met Asn Lys Ile
        275                 280                 285

Pro Ile Glu Ser Ser Gly Arg Ile Asp Val Ile Asp Phe Ser Gln
290                 295                 300

Cys Asp Gly Asp Glu Ile Val Leu Lys Asn Asp Leu Gly Pro Asp Ala
305                 310                 315                 320

Asp Ala Glu Asp Glu Thr Asn Glu Ile Met Lys Phe Lys Val Ser Lys
                325                 330                 335

Pro Leu Lys Glu Lys Asp Thr Ser Val Ile Pro Lys Arg Leu Ser Thr
                340                 345                 350

Ile Arg Ser Leu Arg Asn Asn Lys Ile Ser Thr His Arg Asn Leu Lys
            355                 360                 365

Leu Val Gly Ser Thr Asp Asp Phe Gly Arg Pro Leu Leu Leu Leu Asn
370                 375                 380

Asn Lys Lys Trp Ala Asp Pro Thr Thr Glu Lys Pro Lys Val Gly Asp
385                 390                 395                 400

Thr Glu Val Trp Ser Phe Ile Asn Thr Thr Asp Phe Ala His Pro Met
                405                 410                 415

His Ile His Leu Ile His Phe Gln Val Leu Asp Arg Gln Pro Phe Asp
            420                 425                 430

Leu Glu Arg Tyr Asn His Asp Gly Thr Ile Ile Tyr Thr Gly Pro Pro
            435                 440                 445

Arg Ala Pro Glu Pro Asn Glu Arg Gly Trp Lys Asp Thr Val Ser Ala
        450                 455                 460

Pro Ala Gly Gln Ile Thr Arg Val Ile Gly Thr Phe Ala Pro Tyr Thr
465                 470                 475                 480

Gly Asn Tyr Val Trp His Cys His Ile Leu Glu His Glu Asp His Asp
                485                 490                 495

Met Met Arg Pro Met Lys Val Ile Asp Pro Lys Gln Arg Lys Asp Lys
                500                 505                 510

<210> SEQ ID NO 2
<211> LENGTH: 509
<212> TYPE: PRT
<213> ORGANISM: Bacillus clausii

<400> SEQUENCE: 2

Met Glu Leu Glu Lys Phe Val Asp Pro Met Pro Ile Met Lys Thr Ala
1               5                   10                  15

Ile Pro Lys Lys Thr Ser Lys Asp Gly Asp Tyr Tyr Glu Ile Glu Met
                20                  25                  30

Lys Glu Phe Ser Gln Lys Leu His Arg Asp Leu Asn Pro Thr Arg Leu
            35                  40                  45

Trp Gly Tyr Asp Gly Gln Phe Pro Gly Pro Thr Ile Glu Val Met Arg
        50                  55                  60

Gly Lys Pro Ala Arg Ile Lys Trp Met Asn Asn Leu Pro Asp Thr His
65                  70                  75                  80

```
Phe Leu Pro Ile Asp Arg Ser Ile His His Val Ala His Glu Pro Glu
                85                  90                  95
Val Arg Thr Val Val His Leu His Gly Ser Glu Thr Thr Pro Ala Ser
                100                 105                 110
Asp Gly Tyr Pro Glu Ala Trp Phe Thr Lys Asp Phe Ala Glu Val Gly
                115                 120                 125
Ser Phe Phe Glu Gln Glu Thr Tyr Glu Tyr Pro Asn Asp Gln Arg Ala
    130                 135                 140
Ala Thr Leu Trp Tyr His Asp His Ala Met Gly Ile Thr Arg Leu Asn
145                 150                 155                 160
Val Tyr Ala Gly Leu Ser Gly Leu Tyr Ile Ile Arg Asp Pro Arg Glu
                165                 170                 175
Glu Gln Leu Asn Leu Pro Lys Gly Glu Phe Asp Ile Pro Leu Leu Ile
                180                 185                 190
Gln Asp Arg Ser Phe Asn Asp Asp Gly Ser Leu Phe Tyr Pro Ala Gln
                195                 200                 205
Pro Ala Asn Pro Ala Pro Asn Leu Pro Asn Pro Ser Val Leu Pro Phe
                210                 215                 220
Phe Val Gly Asp Thr Ile Leu Val Asn Gly Lys Val Trp Pro Tyr Leu
225                 230                 235                 240
Gln Val Glu Pro Arg Lys Tyr Arg Phe Arg Ile Leu Asn Gly Ser Asn
                245                 250                 255
Ser Arg Ser Tyr Gln Leu Ala Leu Asp Ser Glu Ala Pro Phe Tyr Gln
                260                 265                 270
Ile Ala Ser Asp Gly Gly Leu Leu Arg Arg Thr Val Ser Leu Gln Ala
                275                 280                 285
Phe Asp Ile Arg Pro Ala Glu Arg Ile Glu Ala Ile Ile Asp Phe Ser
                290                 295                 300
Lys Phe Glu Gly Gln Thr Ile Thr Leu Lys Asn Asn Ala Ser Thr Asp
305                 310                 315                 320
Ala Thr Ala Asp Val Met Gln Phe Gln Val Val Leu Pro Leu Ser Gly
                325                 330                 335
Glu Asp Thr Ser Ile Ile Pro Gln Asn Leu Ser Tyr Ile Pro Ser Leu
                340                 345                 350
Gln Gln Asn Asp Val Lys Arg Ile Arg Asn Leu Lys Ile Ser Gly Thr
                355                 360                 365
Thr Asp Glu Tyr Gly Arg Pro Leu Leu Leu Leu Asn Asn Lys Leu Trp
                370                 375                 380
Ser Asp Pro Val Glu Glu Lys Pro Cys Leu Gly Thr Thr Glu Ile Trp
385                 390                 395                 400
Ser Phe Val Asn Val Thr Asn Val Pro His Pro Met His Ile His Leu
                405                 410                 415
Val Gln Phe Gln Leu Leu Asp His Arg Ala Phe Asn Val Glu Leu Tyr
                420                 425                 430
Asn Glu Asn Gly Gln Ile Glu Leu Val Gly Pro Thr Ile Pro Pro Lys
                435                 440                 445
Ile Asn Glu Arg Gly Trp Lys Asp Thr Ile Thr Ala Pro Ala Gly Gln
                450                 455                 460
Ile Thr Arg Val Ile Ala Arg Phe Ala Pro Phe Ser Gly Tyr Tyr Val
465                 470                 475                 480
Trp His Cys His Ile Leu Glu His Glu Asp Tyr Asp Met Met Arg Pro
                485                 490                 495
```

```
Phe Val Val Ile Asp Pro Lys Thr Glu Lys Glu Arg Arg
            500                 505

<210> SEQ ID NO 3
<211> LENGTH: 513
<212> TYPE: PRT
<213> ORGANISM: Bacillus subtilis

<400> SEQUENCE: 3

Met Thr Leu Glu Lys Phe Val Asp Ala Leu Pro Ile Pro Asp Thr Leu
1               5                   10                  15

Lys Pro Val Gln Gln Thr Thr Glu Lys Thr Tyr Tyr Glu Val Thr Met
            20                  25                  30

Glu Glu Cys Ala His Gln Leu His Arg Asp Leu Pro Pro Thr Arg Leu
        35                  40                  45

Trp Gly Tyr Asn Gly Leu Phe Pro Gly Pro Thr Ile Glu Val Lys Arg
    50                  55                  60

Asn Glu Asn Val Tyr Val Lys Trp Met Asn Asn Leu Pro Ser Glu His
65                  70                  75                  80

Phe Leu Pro Ile Asp His Thr Ile His His Ser Asp Ser Gln His Glu
                85                  90                  95

Glu Pro Glu Val Lys Thr Val Val His Leu His Gly Val Thr Pro
            100                 105                 110

Pro Asp Ser Asp Gly Tyr Pro Glu Ala Trp Phe Ser Lys Asp Phe Glu
        115                 120                 125

Gln Thr Gly Pro Tyr Phe Lys Arg Glu Val Tyr His Tyr Pro Asn Gln
    130                 135                 140

Gln Arg Gly Ala Thr Leu Trp Tyr His Asp His Ala Met Ala Leu Thr
145                 150                 155                 160

Arg Leu Asn Val Tyr Ala Gly Leu Val Gly Ala Tyr Ile Ile His Asp
                165                 170                 175

Pro Lys Glu Lys Arg Leu Lys Leu Pro Ser Gly Glu Tyr Asp Val Pro
            180                 185                 190

Leu Leu Ile Thr Asp Arg Thr Ile Asn Glu Asp Gly Ser Leu Phe Tyr
        195                 200                 205

Pro Ser Gly Pro Glu Asn Pro Ser Pro Ser Leu Pro Lys Pro Ser Ile
    210                 215                 220

Val Pro Ala Phe Cys Gly Asp Thr Ile Leu Val Asn Gly Lys Val Trp
225                 230                 235                 240

Pro Tyr Leu Glu Val Glu Pro Arg Lys Tyr Arg Phe Arg Val Ile Asn
                245                 250                 255

Ala Ser Asn Ala Arg Thr Tyr Asn Leu Ser Leu Asp Asn Gly Gly Glu
            260                 265                 270

Phe Ile Gln Ile Gly Ser Asp Gly Gly Leu Leu Pro Arg Ser Val Lys
        275                 280                 285

Leu Asn Ser Phe Ser Leu Ala Pro Ala Glu Arg Tyr Asp Ile Ile Ile
    290                 295                 300

Asp Phe Thr Ala Tyr Glu Gly Glu Ser Ile Ile Leu Ala Asn Ser Glu
305                 310                 315                 320

Gly Cys Gly Gly Asp Ala Asn Pro Glu Thr Asp Ala Asn Ile Met Gln
                325                 330                 335

Phe Arg Val Thr Lys Pro Leu Ala Gln Lys Asp Glu Ser Arg Lys Pro
            340                 345                 350

Lys Tyr Leu Ala Ser Tyr Pro Ser Val Gln Asn Glu Arg Ile Gln Asn
        355                 360                 365
```

-continued

```
Ile Arg Thr Leu Lys Leu Ala Gly Thr Gln Asp Glu Tyr Gly Arg Val
370                 375                 380

Val Gln Leu Leu Asn Asn Lys Arg Trp His Asp Pro Val Thr Glu Ala
385                 390                 395                 400

Pro Lys Ala Gly Thr Thr Glu Ile Trp Ser Ile Val Asn Pro Thr Gln
                405                 410                 415

Gly Thr His Pro Ile His Leu His Leu Val Ser Phe Arg Val Leu Asp
                420                 425                 430

Arg Arg Pro Phe Asp Ile Ala Arg Tyr Gln Glu Arg Gly Glu Leu Ser
                435                 440                 445

Tyr Thr Gly Pro Ala Val Pro Pro Pro Ser Glu Lys Gly Trp Lys
                450                 455                 460

Asp Thr Ile Gln Ala His Ala Gly Glu Val Leu Arg Ile Ala Val Thr
465                 470                 475                 480

Phe Gly Pro Tyr Ser Gly Arg Tyr Val Trp His Cys His Ile Leu Glu
                485                 490                 495

His Glu Asp Tyr Asp Met Met Arg Pro Met Asp Ile Thr Asp Pro His
                500                 505                 510

Lys

<210> SEQ ID NO 4
<211> LENGTH: 519
<212> TYPE: PRT
<213> ORGANISM: Escherichia coli

<400> SEQUENCE: 4

Met Gln Arg Arg Asp Phe Leu Lys Tyr Ser Val Ala Leu Gly Val Ala
1               5                   10                  15

Ser Ala Leu Pro Leu Trp Asn Arg Ala Val Phe Ala Ala Glu Arg Pro
                20                  25                  30

Thr Leu Pro Ile Pro Asp Leu Leu Thr Thr Asp Ala Arg Asn Arg Ile
            35                  40                  45

Gln Leu Thr Ile Gly Ala Gly Gln Ser Thr Phe Gly Gly Lys Thr Ala
    50                  55                  60

Thr Thr Trp Gly Tyr Asn Gly Asn Leu Leu Gly Pro Ala Val Lys Leu
65                  70                  75                  80

Gln Arg Gly Lys Ala Val Thr Val Asp Ile Tyr Asn Gln Leu Thr Glu
                85                  90                  95

Glu Thr Thr Leu His Trp His Gly Leu Glu Val Pro Gly Glu Val Asp
                100                 105                 110

Gly Gly Pro Gln Gly Ile Ile Pro Pro Gly Gly Lys Arg Ser Val Thr
            115                 120                 125

Leu Asn Val Asp Gln Pro Ala Ala Thr Cys Trp Phe His Pro His Gln
    130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
                165                 170                 175

Gly Ile Asp Asp Val Pro Val Ile Val Gln Asp Lys Lys Phe Ser Ala
                180                 185                 190

Asp Gly Gln Ile Asp Tyr Gln Leu Asp Val Met Thr Ala Ala Val Gly
            195                 200                 205

Trp Phe Gly Asp Thr Leu Leu Thr Asn Gly Ala Ile Tyr Pro Gln His
    210                 215                 220
```

Ala Ala Pro Arg Gly Trp Leu Arg Leu Arg Leu Leu Asn Gly Cys Asn
225                 230                 235                 240

Ala Arg Ser Leu Asn Phe Ala Thr Ser Asp Asn Arg Pro Leu Tyr Val
            245                 250                 255

Ile Ala Ser Asp Gly Gly Leu Leu Pro Glu Pro Val Lys Val Ser Glu
        260                 265                 270

Leu Pro Val Leu Met Gly Glu Arg Phe Glu Val Leu Glu Val Asn
    275                 280                 285

Asp Asn Lys Pro Phe Asp Leu Val Thr Leu Pro Val Ser Gln Met Gly
290                 295                 300

Met Ala Ile Ala Pro Phe Asp Lys Pro His Pro Val Met Arg Ile Gln
305                 310                 315                 320

Pro Ile Ala Ile Ser Ala Ser Gly Ala Leu Pro Asp Thr Leu Ser Ser
                325                 330                 335

Leu Pro Ala Leu Pro Ser Leu Glu Gly Leu Thr Val Arg Lys Leu Gln
            340                 345                 350

Leu Ser Met Asp Pro Met Leu Asp Met Met Gly Met Gln Met Leu Met
        355                 360                 365

Glu Lys Tyr Gly Asp Gln Ala Met Ala Gly Met Asp His Ser Gln Met
    370                 375                 380

Met Gly His Met Gly His Gly Asn Met Asn His Met Asn His Gly Gly
385                 390                 395                 400

Lys Phe Asp Phe His His Ala Asn Lys Ile Asn Gly Gln Ala Phe Asp
                405                 410                 415

Met Asn Lys Pro Met Phe Ala Ala Lys Gly Gln Tyr Glu Arg Trp
            420                 425                 430

Val Ile Ser Gly Val Gly Asp Met Met Leu His Pro Phe His Ile His
        435                 440                 445

Gly Thr Gln Phe Arg Ile Leu Ser Glu Asn Gly Lys Pro Pro Ala Ala
    450                 455                 460

His Arg Ala Gly Trp Lys Asp Thr Val Lys Val Glu Gly Asn Val Ser
465                 470                 475                 480

Glu Val Leu Val Lys Phe Asn His Asp Ala Pro Lys Gly His Ala Tyr
                485                 490                 495

Met Ala His Cys His Leu Leu Glu His Glu Asp Thr Gly Met Met Leu
            500                 505                 510

Gly Phe Thr Val Ser Asp Pro
        515

<210> SEQ ID NO 5
<211> LENGTH: 1539
<212> TYPE: DNA
<213> ORGANISM: Bacillus wakoensis

<400> SEQUENCE: 5

```
atgcgtcgca aactggaaaa atttgttgat agcctgccga ttatggaaac cctgcagccg      60
aaaaccaaag gcaaaaacta ttatgaggtg aaaatccaag agtttaaaaa aaaactgcac     120
cgtgatctgc ctccgaccac cctgtggggt tataatgcac agtttccggg tcgaccatt      180 gaagcaaata gcaatgaacc ggttgaagtg aaatggatta tgagctgcc gaacaaacat     240 tttctgccgg ttgattggag catcatgaat aaagatctgc cggaagttcg tcatgttacc     300
catctgcatg tggtcgtac cccgtgggt agtgatggtt atccgaagc atggtatacg     360 aaagattata agaagtggg cagcttcttc aaagaagagg tttatcgtta tctgaatgaa     420
```

```
cagcgtgcaa tgatgctgtg gtatcatgat cataccatgg gtattacccg tctgaataac      480
tatgcaggtc tggcaggcgc atatatcatt cgtgataaac atgaaaaaag cctgaatctg      540
cctgaaggcg aatatgaagt tccgctgatt attcaggatc gcacctttaa tgaagatggc      600
agcctgtttt atccgaccgg tccggaagat ggcggtgagg atctgccgaa tccgagcatt      660
gttccggcat ttctgggtga taccgttctg gttaatggta agtttggcc gtatctggaa       720 gttgaaccgc gtaaatatcg ttttcgtatt ctgaatggta gcaacacccg tagctatcag      780
ctgcatctgg atagcaatca agaagtgtat cagattggtt cagatggtgg tctgctggaa      840
aaaccggtgc agatgaacaa aattccgatt gaaagcagcg aacgcattga tgtgattatc      900
gattttagcc agtgtgatgg tgatgagatt gtgctgaaaa atgatctggg tccggatgca      960
gatgccgaag atgaaaccaa tgaaatcatg aaattcaaag tgagcaaacc gctgaaagag     1020
aaagatacca gcgttattcc gaaacgtctg agcaccattc gtagcctgcg taataacaaa     1080
attagcaccc atcgtaatct gaaactggtt ggtagcaccg atgattttgg tcgtcctctg     1140
ctgctgctga caacaaaaa atgggcagat ccgaccacag aaaaaccgaa agttggcgat      1200
accgaagttt ggagctttat taacaccacc gattttgcac atccgatgca tattcatctg     1260
atccattttc aggttctgga tcgtcagccg tttgatctgg aacgttataa tcatgatggc     1320
accattatct ataccggtcc gcctcgtgca ccggaaccga tgaacgtggt tggaaagat      1380 acagttagcg caccggcagg tcagattacc cgtgttattg gcacctttgc accgtatacc     1440
ggtaattatg tttggcattg tcatatcctg gaacacgaag atcacgatat gatgcgtccg     1500
atgaaagtta ttgatccgaa acagcgtaaa gataaataa                            1539
```

<210> SEQ ID NO 6
<211> LENGTH: 1530
<212> TYPE: DNA
<213> ORGANISM: Bacillus clausii

<400> SEQUENCE: 6

```
atggaactgg aaaaatttgt tgatccgatg ccgattatga aaaccgccat tccgaaaaaa       60
accagcaaag atggcgatta ttatgagatc gagatgaaag agtttagcca gaaactgcat     120
cgtgatctga atccgacccg tctgtgggt tatgatggtc agtttccggg tccgaccatt      180
gaagttatgc gtggtaaacc ggcacgtatt aaatggatga taatctgcc ggataccccat    240 tttctgccga ttgatcgtag cattcatcat gttgcacatg aaccggaagt tcgtaccgtt     300
gttcatctgc atggtagcga aaccacaccg gcaagtgatg ttatccggga agcatggttt     360
accaaagatt ttgcagaagt gggcagcttt tttgagcaag aaacctatga atatccgaat    420
gatcagcgtg cagcaaccct gtggtatcat gatcacgcaa tgggtattac ccgtctgaat    480
gtttatgcag gtctgagcgg tctgtatatt atccgtgatc gcgtgaaga acagctgaat     540 ctgccgaaag tgaatttga tattccgctg ctgattcagg atcgcagctt taatgatgat    600
ggtagcctgt tttatccggc acagcctgca aatccggcac cgaacctgcc gaatccgagc    660
gttctgccgt ttttttgtt tgataccatt ctggttaatg gtaaagtttg gccgtatctg     720
caggttgaac cgcgtaaata tcgttttcgt attctgaatg gtagcaacag ccgtagctat    780
cagctggcac tggatagcga agccaccgttt tatcagattg catcagatgg tggtctgctg    840
cgtcgtaccg tgagtctgca ggcatttgat atccgtcctg cagaacgtat tgaagccatt    900 atcgattta gcaaatttga gggtcagacc atcaccctga aaaataacgc aagcaccgat    960
```

-continued

```
gcaaccgcag atgttatgca gttccaggtt gttctgccgc tgagcggtga agataccagc    1020
attattccgc agaatctgag ctatattccg agcctgcagc agaatgatgt taaacgtatt    1080
cgcaacctga aaattagcgg caccaccgat gaatatggtc gtcctctgct gctgctgaat    1140
aacaaactgt ggtcagatcc ggttgaagaa aaaccgtgtc tgggtacaac cgaaatttgg    1200
agctttgtta atgttaccaa tgttccgcat ccgatgcata tccatctggt tcagtttcag    1260
ctgctggatc atcgtgcatt taatgtggaa ctgtataatg aaaacggcca gattgaactg    1320
gttggtccga caattcctcc gaaaattaac gaacgtggtt ggaaagatac cattaccgca    1380
ccggcaggtc agattacccg tgttattgca cgttttgcac cgtttagcgg ttattatgtt    1440
tggcattgtc atatcctgga acacgaggat tatgatatga tgcgtccgtt tgttgtgatt    1500
gatccgaaaa ccgaaaaaga acgtcgctaa                                     1530
```

<210> SEQ ID NO 7
<211> LENGTH: 1542
<212> TYPE: DNA
<213> ORGANISM: Bacillus subtilis

<400> SEQUENCE: 7

```
atgacacttg aaaaatttgt ggatgctctc ccaatcccag atacactaaa gccggtgcag      60
caaacaacag aaaaaacata ctacgaagtc accatggaag aatgcgccca tcagcttcac     120
cgcgatctcc ctccgacccg cctgtggggc tacaacggct tatttcccgg gcctaccatt     180
gaggtcaaaa gaaacgaaaa cgtgtatgta aaatggatga caaccttcc gtcagagcat     240 ttccttccga tcgatcacac gattcatcac agtgacagcc agcatgaaga gccagaagta     300
aagactgtcg ttcatttaca cggaggcgtc acgccaccgg atagtgacgg gtatccagag     360
gcttggtttt ctaaagactt tgaacaaaca ggcccttatt ttaaacgaga ggtttatcat     420
tatccgaatc agcaacgcgg tgctaccttg tggtatcacg atcacgccat ggcgctcacc     480
aggctgaatg tctatgccgg acttgttggc gcgtatatta ttcacgatcc aaaggaaaaa     540
cgcctaaagc tgccttccgg cgaatacgac gtgccgcttc ttatcacaga ccgcacgatc     600
aatgaggacg ttctctttgtt ttatccaagc ggaccggaaa acccttcccc gtcactgcct     660
aaaccttcaa tcgttccggc ttttgcgga cacaccatac tcgtcaacgg aaggtatgg     720 ccatacttgg aggtcgaacc gaggaaatac cgcttccgcg tcatcaacgc ctccaatgct     780
agaacctata acctgtcact cgataatggc ggagaattta ttcagattgg ttcagacggg     840
gggctcctgc cgcgctctgt taaactgaac tctttcagtc ttgcgcccgc tgaacgttac     900
gatatcatca ttgacttcac agcatacgaa ggagaatcga tcattttggc aaacagcgag     960
ggctgcggag gtgacgctaa tccagaaaca gatgcgaata tcatgcaatt cagagtcacc    1020
aaaccgttgg cacaaaaaga tgaaagcaga agccaaagt accttgcctc ataccttcc     1080 gtacagaatg aaagaataca aaacatcaga cactgaaac tggcaggcac ccaggacgaa    1140
tacggcagag ttgtccagct gcttaataac aaacgctggc acgatcctgt cacagaagca    1200
ccaaaagccg gcacaactga aatttggtcc atcgtcaacc cgacgcaagg aacacatccg    1260
attcacctgc atttggtctc cttccgtgtg ttggaccggc gtccgtttga tatcgcgcgt    1320
tatcaagaaa gagggggaatt gtcctatacc ggtccggctg ttccgccgcc gccaagtgaa    1380
aaaggctgga agacaccat ccaagcacat gcaggtgaag tcctgagaat cgcggtgaca    1440 ttcggaccctt acagcggacg atacgtatgg cactgccata ttcttgagca tgaagactat    1500
gacatgatga gaccgatgga tataactgat ccccataaat aa                        1542
```

```
<210> SEQ ID NO 8
<211> LENGTH: 1560
<212> TYPE: DNA
<213> ORGANISM: Escherichia coli

<400> SEQUENCE: 8
atgcaacgtc gtgatttctt aaaatattcc gtcgcgctgg gtgtggcttc ggctttgccg      60
ctgtggaacc gcgcagtatt tgcggcagaa cgcccaacgt taccgatccc tgatttgctc     120
acgaccgatg cccgtaatcg cattcagtta actattggcg caggccagtc cacctttggc     180
gggaaaactg caactacctg gggctataac ggcaatctgc tggggccggc ggtgaaatta     240
cagcgcggca aagcggtaac ggttgatatc tacaaccaac tgacggaaga gacaacgttg     300
cactggcacg ggctggaagt accggtgaa gtcgacggcg gcccgcaggg aattattccg     360
ccaggtggca agcgctcggt gacgttgaac gttgatcaac ctgccgctac ctgctggttc     420
catccgcatc agcacggcaa aaccgggcga caggtggcga tggggctggc tgggctggtg     480
gtgattgaag atgacgagat cctgaaatta atgctgccaa acagtgggg tatcgatgat     540 gttccggtga tcgttcagga taagaaattt agcgccgacg ggcagattga ttatcaactg     600
gatgtgatga ccgccgccgt gggctggttt ggcgatacgt tgctgaccaa cggtgcaatc     660
tacccgcaac acgctgcccc gcgtggttgg ctgcgcctgc gtttgctcaa tggctgtaat     720
gcccgttcgc tcaatttcgc caccagcgac aatcgcccgc tgtatgtgat tgccagcgac     780
ggtggtctgc tacctgaacc agtgaaggtg agcgaactgc cggtgctgat gggcgagcgt     840
tttgaagtgc tggtggaggt taacgataac aaaccctttg acctggtgac gctgccggtc     900
agccagatgg ggatggcgat tgcgccgttt gataagcctc atccggtaat gcggattcag     960
ccgattgcta ttagtgcctc cggtgctttg ccagacacat taagtagcct gcctgcgtta    1020
ccttcgctgg aagggctgac ggtacgcaag ctgcaactct ctatggaccc gatgctcgat    1080
atgatgggga tgcagatgct aatggagaaa tatggcgatc aggcgatggc cgggatggat    1140
cacagccaga tgatgggcca tatggggcac ggcaatatga atcatatgaa ccacggcggg    1200
aagttcgatt tccaccatgc caacaaaatc aacggtcagg cgtttgatat gaacaagccg    1260
atgtttgcgg cggcgaaagg gcaatacgaa cgttgggtta tctctggcgt gggcgacatg    1320
atgctgcatc cgttccatat ccacggcacg cagttccgta tcttgtcaga aaatggcaaa    1380
ccgccagcgg ctcatcgcgc gggctggaaa gataccgtta aggtagaagg taatgtcagc    1440
gaagtgctgc tgaagtttaa tcacgatgca ccgaaagaac atgcttatat ggcgcactgc    1500
catctgctgg agcatgaaga tacggggatg atgttagggt ttacggtatc ggatccttaa    1560
```

METHOD FOR LIGNIN DEPOLYMERISATION

FIELD OF THE INVENTION

The present invention is in the field of depolymerisation of lignin. Preferably, the depolymerisation is performed by an enzyme, in particular a laccase, more in particular a laccase with an amino acid sequence according to SEQ ID NO: 1 or an analogue thereof. Such a process is useful in the production of depolymerised lignin that can be more easily processed into various products, in comparison to the high molecular weight lignin before depolymerisation. Examples of useful products that can be prepared from depolymerised lignin are binders, adhesives, dispersants, packaging material, bioplastics (PHA), lipid, asphalt binder, and carbon fiber.

The present invention is also useful in the field of delignifying and/or bleaching of pulp, more in particular wood pulp. Such a process is useful in paper production. The invention therefore also relates to the use of an enzyme for delignification and/or bleaching, in particular a bacterial laccase, more in particular a laccase with an amino acid sequence according to SEQ ID NO: 1 or an analogue thereof.

BACKGROUND OF THE INVENTION

Pulp is a composition comprising lignocellulosic fibrous material prepared by chemically or mechanically separating cellulose fibers from biomass, such as wood, fiber crops or waste paper. The timber resources used to make wood pulp are referred to as pulpwood. Wood pulp comes from softwood trees such as spruce, pine, fir, larch and hemlock, and hardwoods such as eucalyptus, aspen and birch.

A pulp mill is a manufacturing facility that converts wood chips or other plant fiber source into a thick fiberboard which can be shipped to a paper mill for further processing. Alternatively, pulp and paper facilities may be integrated and wet pulp mass can be used directly for paper production.

Pulp is characterized by its ability to absorb and retain water, which may be quantified as Canadian Standard Freeness (CSF) measured in milliliters. Defibrated wood material can be considered as pulp if its CSF can be determined.

Pulp can be manufactured using mechanical, semi-chemical or fully chemical methods (Kraft and sulfite processes). The finished product may be either bleached or non-bleached, depending on the customer's requirements.

Wood and other plant materials that may be used to make pulp contain three main components (apart from water): cellulose fibers (desired for papermaking), lignin (a three-dimensional polymer that binds the cellulose fibers together) and hemicelluloses, (shorter branched carbohydrate polymers).

The aim of the pulping process is to break down the bulk structure of the fiber source, be it chips, stems or other plant parts, into the constituent fibers.

Chemical pulping such as Kraft pulping achieves this by chemically degrading the lignin and hemicellulose into small, water-soluble molecules which can be washed away from the cellulose fibers without depolymerizing the cellulose fibers. However, this process of chemically depolymerizing the hemicellulose weakens the fibers.

The Kraft process (also known as kraft pulping or sulfate process) is a process for conversion of wood into wood pulp, which consists of almost pure cellulose fibers. The Kraft process entails treatment of wood chips with a hot mixture of water, sodium hydroxide, and sodium sulfide, known as white liquor, which breaks the bonds that link lignin, hemicellulose, and cellulose. The technology entails several steps, both mechanical and chemical. It is the dominant method for producing paper.

The various mechanical pulping methods, such as groundwood (GW) and refiner mechanical pulping (RMP), physically tear the cellulose fibers one from another. Much of the lignin remains adhered to the fibers. Strength may also be impaired because the fibers may be cut.

There are a number of related hybrid pulping methods that use a combination of chemical and thermal treatment, for instance an abbreviated chemical pulping process, followed immediately by a mechanical treatment to separate the fibers. These hybrid methods include chemi-thermomechanical pulping, also known as CTMP. The chemical and thermal treatments reduce the amount of energy subsequently required by the mechanical treatment, and also reduce the loss of strength suffered by the fibers.

Mechanical pulping of wood is extremely energy intensive process; for example, a typical newsprint pulp may need 2160 kWh of refiner energy per ton of feedstock to refine wood chips into pulp. Reducing this energy requirement is a very acute need of the industry.

Lignin is the second most abundant biopolymer on the earth and a major component of the plant cell wall. Lignin is also a major waste product for several industries, including the paper and pulping industry and the lignocellulosic biorefinery. Due to the recalcitrant nature of the complex polyphenolic structure, the utilization of lignin for the production of biofuels and bioproducts is a major challenge for both biorefineries and paper/pulping industry. As compared to cellulose and hemicellulose, the methods and systems for utilization of lignin are very limited.

As one of the solutions, enzymes capable of oxidizing lignin were proposed to be used for pretreatment of wood chips in order to decrease the energy required for grinding. This idea was perceived from natural observation that fungi, especially white-rot fungi are able to decay wood material by secreting lignolytic enzymes such as peroxidases and laccases.

This idea was first implemented as so-called bio-pulping, when fungal species were actually cultivated on wood chips before pulping. This resulted in substantial energy saving, but cultivation time comprised several weeks, which was not acceptable in industrial context.

Subsequently, it was proposed to use isolated enzyme preparations for wood pretreatment, rather than live species, which should in principle produce similar effect. This resulted in a limited number of publications wherein isolated fungal enzymes, such as laccases and xylanases were employed for wood chips pretreatment.

Bleaching of wood pulp is the chemical processing carried out on various types of wood pulp to decrease the color of the pulp, so that it becomes whiter. This process requires degradation or removal of the residual lignin, which causes the color. The main use of wood pulp is to make paper where whiteness or "brightness" is an important characteristic. The processes and chemistry described herein are also applicable to the bleaching of non-wood pulps, such as those made from bamboo or kenaf.

Brightness is a measure of how much light is reflected by paper under specified conditions and is usually reported as a percentage of how much light is reflected, so a higher number represents a brighter or whiter paper.

Whereas the results are the same, the processes and fundamental chemistry involved in bleaching chemical pulps (like kraft or sulfite) are very different from those involved in bleaching mechanical pulps (like stoneground, thermomechanical or chemithermomechanical). Chemical pulps contain very little lignin while mechanical pulps contain most of the lignin that was present in the wood used to make the pulp. Lignin is the main source of color in pulp due to the presence of a variety of chromophores naturally present in the wood or created in the pulp mill.

Mechanical pulp retains most of the lignin present in the wood used to make the pulp and thus contain almost as much lignin as they do cellulose and hemicellulose. It would be impractical to remove this much lignin by bleaching, and undesirable since one of the big advantages of mechanical pulp is the high yield of pulp based on wood used. Therefore, the objective of bleaching mechanical pulp (also referred to as brightening) is to remove only the chromophores (color-causing groups). This is possible because the structures responsible for color are also more susceptible to oxidation or reduction.

Alkaline hydrogen peroxide is the most commonly used bleaching agent for mechanical pulp. The amount of base such as sodium hydroxide is less than that used in bleaching chemical pulps and the temperatures are lower. These conditions allow alkaline peroxide to selectively oxidize non-aromatic conjugated groups responsible for absorbing visible light. The decomposition of hydrogen peroxide is catalyzed by transition metals, and iron, manganese and copper are of particular importance in pulp bleaching. The use of chelating agents like EDTA to remove some of these metal ions from the pulp prior to adding peroxide allows the peroxide to be used more efficiently. Magnesium salts and sodium silicate are also added to improve bleaching with alkaline peroxide.

Sodium dithionite (Na2S2O4), also known as sodium hydrosulfite, is the other main reagent used to brighten mechanical pulps. In contrast to hydrogen peroxide, which oxidizes the chromophores, dithionite reduces these color-causing groups. Dithionite reacts with oxygen, so efficient use of dithionite requires that oxygen exposure be minimized during its use.

The brightness gains achieved in bleaching mechanical pulps are temporary since almost all of the lignin present in the wood is still present in the pulp. Exposure to air and light can produce new chromophores from this residual lignin. This is why newspaper yellows as it ages.

Chemical pulps, such as those from the kraft process or sulfite pulping, contain much less lignin than mechanical pulps, (<5% compared to approximately 40%). The goal in bleaching chemical pulps is to remove essentially all of the residual lignin, hence the process is often referred to as delignification. Sodium hypochlorite (household bleach) was initially used to bleach chemical pulps, but was largely replaced in the 1930s by chlorine. Concerns about the release of organochlorine compounds into the environment prompted the development of Elemental Chlorine Free (ECF) and Totally Chlorine Free (TCF) bleaching processes.

A variety of other bleaching agents have been used on chemical pulps. They include peroxyacetic acid, peroxyformic acid, potassium peroxymonosulfate (Oxone) and dimethyldioxirane which is generated in situ from acetone and potassium peroxymonosulfate, and peroxymonophosphoric acid.

Enzymes have also been proposed for use in pulp bleaching, mainly to increase the efficiency of other bleaching chemicals. It has been suggested that the process of delignification of the pulp (removing lignin to achieve white color) can be supported by oxidoreductase enzymes such as laccases.

Laccase-catalyzed oxidative delignification of kraft pulp possibly offers some potential as a replacement or booster for conventional chemical bleaching (Bourbonnais et al., 1997, "Reactivities of Various Mediators and Laccases with Kraft Pulp and Lignin Model Compounds". Appl. Environmental Microbiol. 63: 4627-4632).

However, at present, the use of commercially available laccases is hampered because they work only in acidic conditions and ambient temperatures, whereas chemical pulping such as Kraft pulping, as well as bleaching is carried out in alkaline conditions and elevated temperatures. Most if not all commercially available laccases are of fungal origin and oxidise substrates only in acidic or neutral conditions. This requires the acidification of pulp after the bleaching process in order for the laccases to work.

There is a need for improved reagents depolymerizing lignin or bleaching reagents, in particular enzymes that work and are stable in alkaline conditions.

SUMMARY OF THE INVENTION

The invention relates to a method of lignin depolymerization, comprising an enzymatic treatment step of contacting a solution or suspension comprising lignin with a laccase at alkaline pH, wherein the laccase has an amino acid sequence according to SEQ ID NO: 1 or an amino acid sequence at least 90% identical to SEQ ID NO: 1 and wherein the lignin is depolymerized. In a preferred embodiment, the invention relates to a method for delignifying or bleaching of a pulp, comprising an enzymatic treatment step wherein lignin-containing pulp and a laccase are reacted at alkaline pH, wherein the laccase has an amino acid sequence according to SEQ ID NO: 1 or an amino acid sequence at least 90% identical to SEQ ID NO: 1.

DETAILED DESCRIPTION OF THE INVENTION

Bacterial laccases have been described to oxidize phenolic compounds in alkaline conditions. We have therefore tested several of such laccases and found that all of them were highly unstable in solution at high alkaline pH (such as pH 9-11) and elevated temperatures.

The bacterial laccases initially tested herein were from *Bacillus wakoensis* (SEQ ID NO: 1), *B. clausii* (SEQ ID NO: 2), *B. subtilis* (SEQ ID NO: 3) and *Escherichia coli* (SEQ ID NO: 4). Although all of these bacterial laccases showed some initial activity at pH 9-11, they are highly unstable under this condition, especially at elevated temperatures such as 40-70 degrees Celsius (FIG. 1).

We then tested several other known bacterial laccases (table 1) and found that every enzyme tested lost more than 50% of its activity after one hour of incubation at pH 11 and 70 degrees Celsius. Total loss of activity was observed after 3-4 hours of incubation at these conditions for all laccases tested. It may therefore be easily concluded that bacterial laccases are not suitable for delignifying or bleaching of a pulp, comprising a step of reacting lignin-containing pulp and a laccase at alkaline pH, such as a pH of 9-11.

Figure 2:
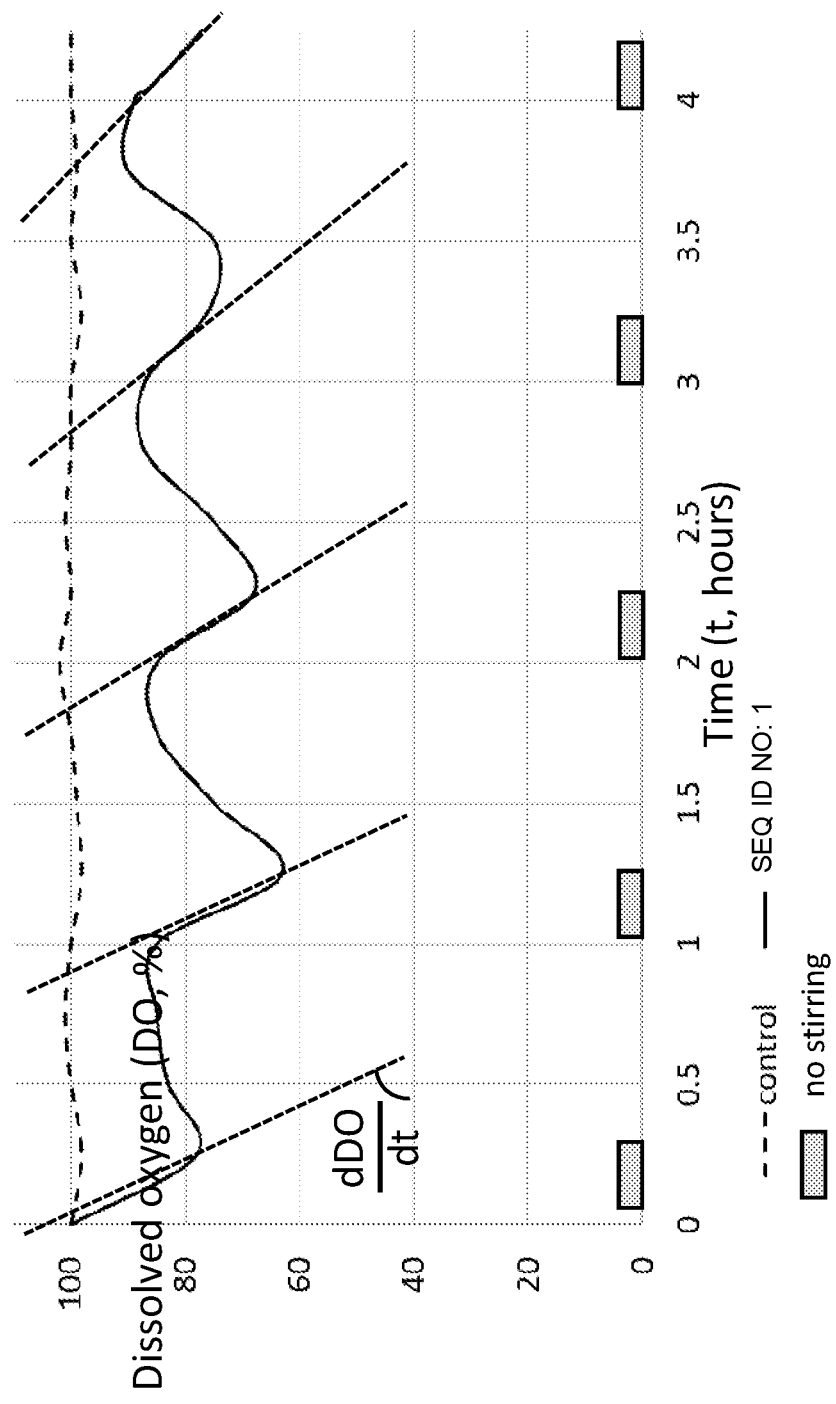

Surprisingly however, we found that a particular laccase (according to SEQ ID NO: 1, obtained from *Bacillus wakoensis*) although quickly inactivated when tested in solution at high temperature and pH, was remarkably stable at pH 9-11 and at 40-70 degrees Celsius in the presence of lignin or lignocellulosic material such as pulp, more in particular wood pulp (FIGS. 2 and 3).

This finding opens up the possibility to use this enzyme and its analogues for depolymerizing lignin at alkaline pH. Hence, the invention relates to a method of lignin depolymerization, comprising an enzymatic treatment step of contacting lignin with a laccase in a solution or suspension at alkaline pH, wherein the laccase has an amino acid sequence according to SEQ ID NO: 1 or an amino acid sequence at least 90% identical to SEQ ID NO: 1 and wherein the lignin is depolymerized.

This finding also opens up the possibility to use this enzyme and its analogues for delignifying and/or bleaching of pulp at alkaline pH.

As used herein, the term "delignifying" refers to a process wherein the lignin in lignin-containing material is degraded or depolymerized resulting in a lower molecular weight of the lignin and an increased solubility of the lignin.

Hence, the invention also relates to a method for delignifying and/or bleaching of a pulp, comprising an enzymatic treatment step wherein lignin-containing pulp and a laccase are reacted at alkaline pH, wherein the laccase has an amino acid sequence according to SEQ ID NO: 1 or an amino acid sequence at least 90% identical to SEQ ID NO: 1.

TABLE 1

Laccases tested for stability at pH11, 70 degrees C. for 1-4 hours.

| No: | Description | Accession No: |
|---|---|---|
| 1 | laccase [*Bacillus subtilis*] | AGZ16504.1 |
| 2 | spore copper-dependent laccase (outer coat) [*Bacillus subtilis* subsp. *spizizenii* str. W23] > ref|WP_003219376.1| copper oxidase [*Bacillus subtilis*] > gb|EFG93543.1| spore copper-dependent laccase [*Bacillus subtilis* subsp. *spizizenii* ATCC 6633] > gb|ADM36695.1| spore copper-dependent laccase (outer coat) [*Bacillus subtilis* subsp. *spizizenii* str. W23] | YP_003865004.1 |
| 3 | spore copper-dependent laccase [*Bacillus subtilis*] > gb|ELS60660.1| spore copper-dependent laccase [*Bacillus subtilis* subsp. *inaquosorum* KCTC 13429] | WP_004397739.1 |
| 4 | copper oxidase [*Bacillus subtilis*] | WP_019713492.1 |
| 5 | laccase [*Bacillus vallismortis*] | AGR50961.1 |
| 6 | spore coat protein A [*Bacillus subtilis* XF-1] > ref|WP_015382982.1| spore coat protein A [*Bacillus*] > gb|AGE62493.1| spore coat protein A [*Bacillus subtilis* XF-1] > gb|ERI42893.1| copper oxidase [*Bacillus* sp. EGD-AK10] | YP_007425830.1 |
| 7 | spore copper-dependent laccase [*Bacillus subtilis* BSn5] > ref|YP_005559844.1| spore coat protein A [*Bacillus subtilis* subsp. natto BEST195] > ref|YP_007210655.1| Spore coat protein A [*Bacillus subtilis* subsp. *subtilis* str. BSP1] > ref|WP_014479048.1| copper oxidase [*Bacillus subtilis*] > dbj|BAI84141.1| spore coat protein A [*Bacillus subtilis* subsp. natto BEST195] > gb|ADV95614.1| spore copper-dependent laccase [*Bacillus subtilis* BSn5] > gb|ADZ57279.1| laccase [*Bacillus* sp. LS02] > gb|ADZ57280.1| laccase [*Bacillus* sp. LS03] > gb|ADZ57283.1| laccase [*Bacillus* sp. WN01] > gb|ADZ57284.1|laccase [*Bacillus subtilis*] > gb|AGA20638.1| Spore coat protein A [*Bacillus subtilis* subsp. *subtilis* str. BSP1] | YP_004206641.1 |
| 8 | CotA [*Bacillus* sp. JS] > ref|WP_014663045.1| copper oxidase [*Bacillus* sp. JS] > gb|AFI27241.1| CotA [*Bacillus* sp. JS] | YP_006230497.1 |
| 9 | copper oxidase [*Bacillus subtilis* QH-1] | EXF51833.1 |
| 10 | copper oxidase [*Bacillus subtilis*] > gb|EHA29133.1| spore copper-dependent laccase [*Bacillus subtilis* subsp. *subtilis* str. SC-8] | WP_003234000.1 |
| 11 | outer spore coat copper-dependent laccase [*Bacillus subtilis* Q6928] > ref|WP_014906195.1| copper oxidase [*Bacillus subtilis*] > dbj|BAA22774.1| spore coat proein A [*Bacillus subtilis*] > gb|AFQ56549.1| Outer spore coat copper-dependent laccase [*Bacillus subtilis* QB928] | YP_006628799.1 |
| 12 | spore coat protein A [*Bacillus subtilis* subsp. *subtilis* str. 168] | NP_388511.1 |
| 13 | spore coat protein A [*Bacillus subtilis* subsp. *subtilis* str. BAB-1] > ref|WP_015482891.1| spore coat protein A [*Bacillus subtilis*] > gb|AGI27890.1| spore coat protein A [*Bacillus subtilis* subsp. *subtilis* str. BAB-1] | YP_007661398.1 |
| 14 | spore coat protein [*Bacillus subtilis*] | ACS44284.1 |
| 15 | spore coat protein [*Bacillus subtilis*] | AGK12417.1 |
| 16 | laccase [*Bacillus* sp. ZW2531-1] | AFN66123.1 |
| 17 | laccase [*Bacillus* sp. HR03] | ACM46021.1 |
| 18 | copper oxidase [*Bacillus vallismortis*] | WP_010329056.1 |
| 19 | laccase [*Bacillus subtilis*] | AEK80414.1 |
| 20 | copper oxidase [*Bacillus mojavensis*] | WP_010333230.1 |
| 21 | CotA [*Bacillus subtilis*] | AAB62305.1 |
| 22 | spore copper-dependent laccase [*Bacillus atrophaeus* 1942] > ref|WP_003328493.1| copper oxidase [*Bacillus atrophaeus*] > gb|ADP31092.1| spore copper-dependent laccase (outer coat) [*Bacillus atrophaeus* 1942] > gb|EIM09308.1| spore copper-dependent laccase [*Bacillus atrophaeus* C89] | YP_003972023.1 |

TABLE 1-continued

Laccases tested for stability at pH11, 70 degrees C. for 1-4 hours.

| No: | Description | Accession No: |
|---|---|---|
| 23 | Spore coat protein A [*Bacillus atrophaeus*] > gb|EOB38473.1| Spore coat protein A [*Bacillus atrophaeus* UCMB-5137] | WP_010787813.1 |
| 24 | copper oxidase [*Bacillus* sp. 5B6] > gb|EIF12180.1| CotA [*Bacillus* sp. 5B6] | WP_007609818.1 |
| 25 | outer spore coat copper-dependent laccase [*Bacillus amyloliquefaciens* subsp. *plantarum* UCMB5036] > ref|YP_008411651.1| outer spore coat copper-dependent laccase [*Bacillus amyloliquefaciens* subsp. *plantarum* UCMB5033] > ref|YP_008420054.1| outer spore coat copper-dependent laccase [*Bacillus amyloliquefaciens* subsp. *plantarum* UCMB5113] > ref|WP_015416957.1| outer spore coat copper-dependent laccase [*Bacillus amyloliquefaciens*] > emb|CCP20645.1| outer spore coat copper-dependent laccase [*Bacillus amyloliquefaciens* subsp. *plantarum* UCMB5036] > emb|CDG28620.1| outer spore coat copper-dependent laccase [*Bacillus amyloliquefaciens* subsp. *plantarum* UCMB5033] > emb|CDG24919.1| outer spore coat copper-dependent laccase [*Bacillus amyloliquefaciens* subsp. *plantarum* UCMB5113] | YP_007496315.1 |
| 26 | spore coat protein CotA [*Bacillus amyloliquefaciens* subsp. *plantarum* YAU B9601-Y2] > ref|YP_006327430.1| spore coat protein A [*Bacillus amyloliquefaciens* Y2] > ref|WP_014417082.1| copper oxidase [*Bacillus amyloliquefaciens*] > gb|ADZ57285.1| laccase [*Bacillus* sp. LC02] > emb|CCG48602.1| spore coat protein CotA [*Bacillus amyloliquefaciens* subsp. *plantarum* YAU B9601-Y2] > gb|AFJ60705.1| spore coat protein A [*Bacillus amyloliquefaciens* Y2] > dbj|BAM49543.1| spore copper-dependent laccase [*Bacillus subtilis* BEST7613] > dbj|BAM56813.1| spore copper-dependent laccase [*Bacillus subtilis* BEST7003] | YP_005419918.1 |
| 27 | spore coat protein A [*Bacillus amyloliquefaciens* subsp. *plantarum* AS43.3] > ref|WP_015239305.1| spore coat protein A [*Bacillus amyloliquefaciens*] > gb|AFZ89646.1| spore coat protein A [*Bacillus amyloliquefaciens* subsp. *plantarum* AS43.3] | YP_007185316.1 |
| 28 | CotA [*Bacillus amyloliquefaciens* subsp. *plantarum* str. FZB42] > ref|YP_008725930.1| cotA [*Bacillus amyloliquefaciens* CC178] > ref|WP_012116986.1| copper oxidase [*Bacillus amyloliquefaciens*] > gb|ABS73055.1| CotA [*Bacillus amyloliquefaciens* subsp. *plantarum* str. FZB42] > gb|AGZ55352.1| cotA [*Bacillus amyloliquefaciens* CC178] | >YP_001420286.1 |
| 29 | laccase [*Bacillus* sp. LC03] | ADZ57286.1 |
| 30 | copper oxidase [*Bacillus* sp. 916] > gb|EJD67619.1| CotA [*Bacillus* sp. 916] | WP_007408880.1 |
| 31 | copper oxidase [*Bacillus amyloliquefaciens*] > gb|ERH51073.1| copper oxidase [*Bacillus amyloliquefaciens* EGD-AQ14] | WP_021495201.1 |
| 32 | copper oxidase [*Bacillus amyloliquefaciens* subsp. *plantarum* TrigoCor1448] | AHK48246.1 |
| 33 | spore copper-dependent laccase [*Bacillus amyloliquefaciens* DSM 7] > ref|YP_005540261.1| spore copper-dependent laccase [*Bacillus amyloliquefaciens* TA208] > ref|YP_005544441.1| spore copper-dependent laccase [*Bacillus amyloliquefaciens* LL3] > ref|YP_005548603.1| spore copper-dependent laccase [*Bacillus amyloliquefaciens* XH7] > ref|WP_013351262.1| copper oxidase [*Bacillus amyloliquefaciens*] > emb|CBI41748.1| spore copper-dependent laccase [*Bacillus amyloliquefaciens* DSM 7] > gb|AEB22768.1| spore copper-dependent laccase [*Bacillus amyloliquefaciens* TA208] > gb|AEB62213.1| spore copper-dependent laccase [*Bacillus amyloliquefaciens* LL3] > gb|AEK87755.1| spore copper-dependent laccase [*Bacillus amyloliquefaciens* XH7] | YP_003919218.1 |
| 34 | copper oxidase [*Bacillus siamensis*] | WP_016937040.1 |
| 35 | outer spore coat protein CotA [*Bacillus sonorensis*] > gb|EME75462.1| outer spore coat protein CotA [*Bacillus sonorensis* L12] | WP_006637314.1 |
| 36 | copper oxidase [*Bacillus* sp. M 2-6] > gb|EIL85237.1| outer spore coat protein A [*Bacillus* sp. M 2-6] | WP_008344352.1 |
| 37 | spore copper-dependent laccase [*Bacillus stratosphericus*] > gb|EMI14845.1| spore copper-dependent laccase [*Bacillus stratosphericus* LAMA 585] | WP_007496963.1 |
| 38 | copper oxidase [*Bacillus pumilus*] | WP_017359847.1 |
| 39 | CotA [*Bacillus pumilus*] | AEX93437.1 |
| 40 | copper oxidase [*Bacillus pumilus*] > gb|EDW21710.1| spore coat protein A [*Bacillus pumilus* ATCC 7061] | WP_003213818.1 |

TABLE 1-continued

Laccases tested for stability at pH11, 70 degrees C. for 1-4 hours.

| No: | Description | Accession No: |
|---|---|---|
| 41 | CotA [*Bacillus pumilus*] | AFL56752.1 |
| 42 | copper oxidase [*Bacillus pumilus*] | WP_019743779.1 |
| 43 | CotA [*Bacillus pumilus*] | AFK33221.1 |
| 44 | outer spore coat protein A [*Bacillus pumilus* SAFR-032] > ref\|WP_012009087.1\| copper oxidase [*Bacillus pumilus*] > gb\|ABV61236.1\| outer spore coat protein A [*Bacillus pumilus* SAFR-032] | YP_001485796.1 |
| 45 | copper oxidase [*Bacillus* sp. HYC-10] > gb\|EKF36812.1\| outer spore coat protein A [*Bacillus* sp. HYC-10] | WP_008355710.1 |
| 46 | copper oxidase [*Bacillus* sp. CPSM8] > gb\|ETB72519.1\| copper oxidase [*Bacillus* sp. CPSM8] | WP_023855578.1 |
| 47 | outer spore coat protein CotA [*Bacillus licheniformis* 9945A] > ref\|WP_020450420.1\| outer spore coat protein CotA [*Bacillus licheniformis*] > gb\|AGN35164.1\| outer spore coat protein CotA [*Bacillus licheniformis* 9945A] | YP_008076901.1 |
| 48 | laccase [*Bacillus* sp. 2008-12-5] | AFP45763.1 |
| 49 | copper oxidase [*Bacillus*] > gb\|EFV71562.1\| CotA protein [*Bacillus* sp. BT1B_CT2] > gb\|ADZ57281.1\| laccase [*Bacillus* sp. LS04] > gb\|EID49890.1\| spore coat protein [*Bacillus licheniformis* WX-02] > gb\|EQM29388.1\| copper oxidase [*Bacillus licheniformis* CG-B52] | WP_003179495.1 |
| 50 | spore coat protein [*Bacillus licheniformis* DSM 13 = ATCC 14580] > ref\|YP_006712087.1\| outer spore coat protein CotA [*Bacillus licheniformis* DSM 13 = ATCC 14580] > ref\|WP_011197606.1\| copper oxidase [*Bacillus licheniformis*] > gb\|AAU22267.1\| spore coat protein (outer) [*Bacillus licheniformis* DSM 13 = ATCC 14580] > gb\|AAU39617.1\| outer spore coat protein CotA [*Bacillus licheniformis* DSM 13 = ATCC 14580] | YP_077905.1 |
| 51 | copper oxidase [*Bacillus licheniformis* S 16] | EWH20929.1 |
| 52 | copper oxidase [*Oceanobacillus kimchii*] | WP_017796468.1 |
| 53 | copper oxidase [*Bacillus* acidiproducens] | WP_018661628.1 |
| 54 | spore outer coat protein [*Oceanobacillus iheyensis* HTE831] > ref\|WP_011065752.1\| copper oxidase [*Oceanobacillus iheyensis*] > dbj\|BAC13302.1\| spore coat protein (outer) [*Oceanobacillus iheyensis* HTE831] | NP_692267.1 |
| 55 | copper oxidase [*Bacillus coagulans*] | WP_017553860.1 |
| 56 | copper oxidase [*Bacillus coagulans*] | WP_019721501.1 |

Mechanical pulp comprises a mix of whole fibers and fiber fragments of different sizes. Paper made from mechanical pulp has a yellowish/grey tone with high opacity and a very smooth surface. Mechanical pulping provides a good yield from the pulpwood because it uses the whole of the log except for the bark, but the energy requirement for refining is high and can only be partly compensated by using the bark as fuel. In subsequent modifications to this process, the woodchips are pre-softened by heat (thermo-mechanical pulping (TMP)) to make the defibration more effective. The resulting pulp is light-coloured and has longer fibers. Thermo-mechanical pulping (TMP) is a process in which wood chips are heated and run through a mechanical refiner for defibration (fiber separation), resulting in thermo-mechanical pulp.

In a typical TMP process, wood chips are fed to a presteamer and are steamed with process steam (typically 1 to 2 bar or above 100 degrees Celsius, such as 130 to 140 degrees C.). Process steam may be obtained from the refiners. After a retention time of several minutes, the pressurized chips may be fed to the refiner with the feeding screw (plug feeder). The refiner separates the fibers by mechanical force via refiner mechanical means (e.g. between rotating disc plates). The refiner may be fed with fresh steam during startup, to increase the pressure up to 4 or 5 bar and about 150 degrees Celsius.

Thermomechanical pulping therefore refers to a process of producing pulp, which includes heating of biomass to a temperature above 100 degrees Celsius and mechanical defibration.

As used herein, thermo-mechanical pulp is pulp produced by processing biomass such as wood chips using heat and a mechanical refining movement.

Wood chips are usually produced as follows: the logs are first stripped of their bark and converted into small chips, which have a moisture content of around 25-30%. A mechanical force is applied to the wood chips in a crushing or grinding action which generates heat and water vapour and softens the lignin thus separating the individual fibers.

The pulp is then screened and cleaned, any material that was not sufficiently refined (did not pass in screening procedure) is separated as "reject" and reprocessed. The TMP process gives a high yield of fiber from the timber (around 95%) and as the lignin has not been removed, the fibers are hard and rigid.

As opposed to mechanical pulping, delignification may also be achieved in a chemical process. A typical example is the so-called "Kraft" delignification process, which uses sodium hydroxide and sodium sulfide to chemically remove lignin. After delignification, the color of the pulp is dark brown. If white paper is desired, the pulp is bleached. Delignified, bleached pulp is fed into paper machines after undergoing other chemical processes that produce the desired quality and characteristics for the paper. A chemical pulp or paper is called wood-free, although in practice a small percentage of mechanical fiber is usually accepted.

Chemical pulping applies so called cooking chemicals to degrade the lignin and hemicellulose into small, water-soluble molecules which can be washed away from the cellulose fibers without depolymerizing the cellulose fibers. This is advantageous because the de-polymerization of cellulose weakens the fibers. Using chemical pulp to produce paper is more expensive than using mechanical pulp or recovered paper, but it has better strength and brightness properties.

A further development of chemical pulping and thermo-mechanical pulping is chemical thermo-mechanical pulping (CTMP). Herein, the wood chips are impregnated with a chemical such as sodium sulphite or sodium hydroxide before the refining step. The end result is a light-coloured pulp with good strength characteristics. The chemical and thermal treatments reduce the amount of energy subsequently required by the mechanical refining, and also reduce the loss of strength suffered by the fibers. In CTMP, wood chips can be pretreated with sodium carbonate, sodium hydroxide, sodium sulfite and other chemicals prior to refining with equipment similar to a mechanical mill. The conditions of the chemical treatment are less vigorous (lower temperature, shorter time, less extreme pH) than in a chemical pulping process since the goal is to make the fibers easier to refine, not to remove lignin as in a fully chemical process.

Wood chips for TMP or CTMP are usually obtained from bark free and fresh tree wood. After manufacturing, the chips are screened to have specified size. For superior quality pulp, and optimal energy consumption, chips usually have thickness of 4-6 mm and length (dimension along the fibers) of 10-50 mm, such as 15-40 mm or 16-22 mm. Before refining, the chips may be washed and steamed, these chips have a typical moisture content of above 20% such as around 25-30%.

In comparison, mechanical pulping requires a lot of energy, in the range of 1000-3500 kiloWatthour per ton of pulp whereas the chemical pulping process is self-sufficient. Chemical pulping yield better (longer) fibers whereas the fibers obtained in mechanical pulping are of different sizes. This results in low paper strength. Production costs of mechanical pulp are much less however in comparison to chemical pulping. Mechanical pulping has a yield of 95% as opposed to 45% of the chemical process. The yield in chemical processes is much lower, as the lignin is completely dissolved and separated from the fibers. However, the lignin from the sulphate and some sulphite processes can be burnt as a fuel oil substitute. In modern mills, recovery boiler operations and the controlled burning of bark and other residues makes the chemical pulp mill a net energy producer which can often supply power to the grid, or steam to local domestic heating plants. Nevertheless, chemical pulping has a stronger negative environmental impact than mechanical pulping due to excessive use of aggressive chemicals.

After grinding, the pulp is sorted by screening to suitable grades. It can then be bleached with peroxide for use in higher value-added products.

As used herein, the term "pulp" is intended to mean a composition comprising lignocellulosic fibrous material prepared by chemically and/or mechanically separating cellulose fibers from wood, fiber crops or waste paper. Pulp is characterized by its ability to absorb water, which can be measured in milliliters as Canadian Standard Freeness (CSF). Pulp is also characterized by the amount of residual lignin, which can be expressed as Kappa number. The Kappa number is a measurement of standard potassium permanganate solution that the pulp will consume, which is determined by a standard protocol ISO 302. Kappa number has a range from 1 to 100, the less lignin, the lower the number. Delignification of lignocellulosic material can be characterized by a decrease in the kappa number. Wood pulp is the most common raw material in papermaking.

The term lignocellulosic material refers to a material that comprises (1) cellulose, hemicellulose, or a combination thereof and (2) lignin.

Laccases (EC 1.10.3.2) are enzymes having a wide taxonomic distribution and belonging to the group of multicopper oxidases. Laccases are eco-friendly catalysts, which use molecular oxygen from air to oxidize various phenolic and non-phenolic lignin-related compounds as well as highly recalcitrant environmental pollutants, and produce water as the only side-product. These natural "green" catalysts are used for diverse industrial applications including the detoxification of industrial effluents, mostly from the paper and pulp, textile and petrochemical industries, use as bioremediation agent to clean up herbicides, pesticides and certain explosives in soil. Laccases are also used as cleaning agents for certain water purification systems. In addition, their capacity to remove xenobiotic substances and produce polymeric products makes them a useful tool for bioremediation purposes.

Laccases were originally discovered in fungi, they are particularly well studied in White-rot fungi and Brown-rot fungi. Later on, laccases were also found in plants and bacteria. Laccases have broad substrate specificity; though different laccases can have somewhat different substrate preferences. Main characteristic of laccase enzyme is its redox potential, and according to this parameter all laccases can be divided in three groups (see, for example, Morozova, O. V., Shumakovich, G. P., Gorbacheva, M. a., Shleev, S. V., & Yaropolov, a. 1. (2007). "Blue" laccases. Biochemistry (Moscow), 72(10), 1136-1150. doi:10.1134/S0006297907100112): high redox potential laccases (0.7-0.8 V), medium redox potential laccases (0.4-0.7 V) and low redox potential laccases (<0.4V). It is believed that low redox potential limits the scope of substrates which the enzyme can possibly oxidize, and vice versa. All high redox potential laccases and the upper part of the medium redox potential laccases are fungal laccases. Industrial application of laccases is mostly if not entirely relying on fungal laccases.

CotA is a bacterial laccase and is a component of the outer coat layers of *bacillus* endospore. It is a 65-kDa protein encoded by the cotA gene (Martins, O., Soares, M., Pereira, M. M., Teixeira, M., Costa, T., Jones, G. H., & Henriques, A. O. (2002). Molecular and Biochemical Characterization of a Highly Stable Bacterial Laccase That Occurs as a Structural Component of the *Bacillus subtilis* Endospore Coat; Biochemistry, 277(21), 18849-18859. doi:10.1074/jbc.M200827200). CotA belongs to a diverse group of multi-copper "blue" oxidases that includes the laccases. This protein demonstrates high thermostability, and resistance to various hazardous elements in accordance with the survival abilities of the endospore. The redox-potential of this protein has been reported to be around 0.5 mV, which places it in the range of medium-redox-potential laccases. CotA laccases are herein also referred to as 'CotA'.

The endospore coat protein CotA is a laccase required for the formation of spore pigment and was recently shown to have also bilirubin oxidase (EC 1.3.3.5) activity. CotA laccases may be very divers with respect to their primary amino acid sequence. The blue copper oxidase CueO enzymes may also be very divers with respect to their primary amino acid sequence.

As used herein, the degree of identity between two or more amino acid sequences is equivalent to a function of the number of identical positions shared by the sequences; i.e., % identity=number of identical positions divided by the total number of aligned positions×100, excluding gaps, which need to be introduced for optimal alignment of the two sequences, and overhangs. The alignment of two sequences is to be performed over the full length of the polypeptides.

The comparison (aligning) of sequences is a routine task for the skilled person and can be accomplished using standard methods known in the art. For example, a freeware conventionally used for this purpose is "Align" tool at NCBI resource found at internet site blast.ncbi.nlm.nih.gov/Blast.cgi?PAGE_TYPE=BlastSearch&BLAST_SPEC=-blast2 seq&LINK_LOC=align2seq, Other commercial and open software such as Vector NTI are also suitable for this purpose.

Optimal dosage may easily be determined by trial and error methods for a given setting in a traditional pulp mill operation. The skilled person will be well aware of methods for optimizing the conditions for optimizing the use of the enzymes as disclosed and described herein. A skilled person will also be well aware of the amount of enzyme to use in order to reach an optimum between effect and costs. The optimal dose of each enzyme may easily be found empirically, and will usually be in the range of 3-1.000.000 microkatal per ton of dry substrate, such as wood. In some preferred embodiments, the lower range of the dose for each enzyme may be at least 5 microkatal per ton of dry substrate, such as 10, 15, 20, 25, 30, 50, 100 or even 300 microkatal per ton of dry substrate.

The teaching as provided herein should not be so narrowly construed as that it relates only to the exemplified sequence of SEQ ID NO: 1. It is well known in the art that protein sequences may be altered or optimized, for instance by site-directed mutagenesis, in order to arrive at proteins with identical or even improved properties. The closest known protein to the *B. wakoensis* laccase is a protein with 64% sequence identity. The sequences of *B. clausii*, *B. subtilis* and *E. coli* exemplified herein are 61, 59 and 24% identical with the sequence according to SEQ ID NO: 1.

Hence, the invention relates to a method as described herein, wherein the laccase has an amino acid sequence at least 90% identical to SEQ ID NO: 1. The term "at least 90%", is to be interpreted as 90%, 91, 92, 93, 94, 95, 96, 97, 98, 99 or more %.

Bleaching of the pulp may be performed by any suitable method know in the art. In a preferred embodiment, the bleaching is performed using peroxide, hydrogen peroxide, oxygen, ozone, chlorine dioxide or a mixture of chlorine dioxide and chlorine gas. Hence, the invention relates to a method as described herein, characterized in that the bleaching of the pulp comprises a step of contacting the pulp with a bleaching chemical selected from the group consisting of peroxide, hydrogen peroxide, oxygen, ozone, chlorine dioxide and a mixture of chlorine dioxide and chlorine gas.

The method of the invention is preferably performed at an elevated temperature. The term "elevated temperature" is to be interpreted as meaning a temperature above 10 degrees Celsius, such as 20, 30, 40, 45, 50 60, 65 or even 70 degrees Celsius. The upper limit for the temperature is determined by the thermostability of the enzyme used and may be as high as 70 degrees, 75, 80, 85 or even 90 degrees Celsius. Hence, in a preferred embodiment, the invention relates to a method as described herein, characterized in that the enzymatic treatment step is carried out at a temperature between 10 and 90 degrees Celsius. Preferably, the temperature of the enzymatic reaction is between 40 and 80 degrees Celsius, such as between 60 and 80 degrees Celsius.

The laccase according to SEQ ID NO: 1 was found to be resistant against heating at 90 degrees Celsius for 4 hours at pH 11 in the presence of lignin or lignocellulosic material such as pulp.

The method according to the invention is preferably performed at an alkaline pH. Hence, in a preferred embodiment, the invention also relates to a method as described herein, characterized in that the pH value of the pulp during the enzymatic treatment is from 7 up to and including 12, such as at a pH value of from 8 up to and including 11, such as at a pH value of 9 up to and including 11 or 12.

The laccase as used in the method according to the invention is preferably a bacterial laccase, such as a laccase obtainable from *Bacillus wakoensis*.

The laccase according to SEQ ID NO: 1 is preferably produced in *Escherichia coli*.

The enzymatic treatment step in a method according to the invention may be performed in the presence or absence of an electron mediator system.

As used here in, an "electron mediator" refers to a chemical compound that can continuously be oxidized by an enzyme and subsequently reduced by the substrate. In particular, an electron mediator in accordance with the invention may refer to a chemical compound that can be oxidized by the laccase enzyme. In general, these mediators are much smaller in molecular size as compared to the laccase enzyme, allowing better penetration of redox reaction components into lignin and reaction with chemical bonds that are not accessible to laccase.

Several of such mediators and systems have been described (Morozova, O. et al., Applied Biochem Microbiol 43: 523-535 (2007). A particularly preferred mediator if required, is syringaldehyde, or an electron mediator selected from the group consisting of 1-hydroxybenzotriazole (HBT), 2,2'-azino-bis-(3-ethylbenzothiazoline-6-sulfonic acid) (ABTS), acetosyringone, phenol, and violuric acid. The method may however also be used without a mediator. This has the advantage that the process is more cost-effective and easier to perform. In a further preferred embodiment, the reaction is performed in the absence of an electron mediator selected from the group consisting of 1-hydroxybenzotriazole (HBT), 2,2'-azino-bis-(3-ethylbenzothiazoline-6-sulfonic acid) (ABTS), acetosyringone, phenol, and violuric acid.

We also found that lignin itself was the compound in pulp that stabilized the enzyme. We therefor repeated the experiments described in examples 3 and 4 with purified high molecular weight (HMW) lignin. The laccase according to SEQ ID NO: 1 was found to be much more stable at pH 9-11 than the alkaline laccases according to SEQ ID NO:s 2-4 in the presence of lignin. This was the case after preincubaton at 40 degrees Celsius as well as at 70 degrees Celsius (Example 6, FIG. 5). The enzyme was able to catalise lignin depolymerisation in solution or suspension under these conditions (Example 6, 7).

The term "purified lignin" is used herein to indicate a dry matter content of 40% or above. This means that when the solution or suspension containing ligning as described above, is fully dried, 40% or more of the remaining dry matter is lignin.

The fact that the stabilizing effect of lignin on the laccase according to SEQ ID NO: 1 could be observed in pulp with a lignin content of 40% as well as with highly purified lignin with a lignin content of about 96%, shows that the stabilizing effect of lignin on the laccase according to SEQ ID NO: 1 is to be expected over a wide range dry-matter content of lignin-containing solutions or suspensions.

The stabilizing effect of lignin was also found over a wide concentration range of lignin. The spruce pulp contained 0.5 grams of lignin per liter, whereas the solution or suspension comprising purified lignin contained 2.2 grams per liter (example 6). It even appeared that the higher the concentration of lignin, the higher the stabilizing effect was.

LEGEND TO THE FIGURES

FIG. 1: Diagram showing residual relative activities (% of initial activity) of different laccases in solution after pre-incubation at:
70 degrees C., at pH 11 for 1-4 hours (FIG. 1A).
70 degrees C., at pH 9 for 1-4 hours (FIG. 1B).
40 degrees C., at pH 11 for 1-4 hours (FIG. 1C).
40 degrees C., at pH 9 for 1-4 hours (FIG. 1D).
Experimental details are provided in Examples 2 and 3.
FIG. 2: Graph showing dissolved oxygen measurements as described in example 4 for delignification of pulp at 70 degrees Celsius and pH 11.
FIG. 3: Diagram showing the stability of different laccases in pulp under different conditions as follows:
70 degrees C., at pH 11 (FIG. 3A).
70 degrees C., at pH 9 (FIG. 3B).
40 degrees C., at pH 11 (FIG. 3C).
40 degrees C., at pH 9 (FIG. 3D).
Experimental details are provided in Example 4.
FIG. 4: Diagram showing the stability of different laccases in purified high molecular weight lignin, under different conditions as follows:
70 degrees C., at pH 11 (FIG. 4A).
70 degrees C., at pH 9 (FIG. 4B).
40 degrees C., at pH 11 (FIG. 4C).
40 degrees C., at pH 9 (FIG. 4D).
Experimental details are provided in Example 6
FIG. 5: Diagram showing the decrease in Kappa numbers (K(start)–K (end)) of the pulps obtained in delignification experiments with different laccases as described in Example 4. The decrease in Kappa number is a measure of delignification of the pulp.

CONCLUDING REMARKS

In conclusion, the invention may be described in the following terms:
1. Method for delignifying and/or bleaching of a pulp, comprising an enzymatic treatment step wherein lignin-containing pulp and a laccase are reacted at alkaline pH, wherein the laccase has an amino acid sequence according to SEQ ID NO: 1 or an amino acid sequence at least 90% identical to SEQ ID NO: 1.
2. Method as described above, characterized in that the bleaching of the pulp comprises a step of contacting the pulp with a bleaching chemical selected from the group consisting of peroxide, hydrogen peroxide, oxygen, ozone, chlorine dioxide and a mixture of chlorine dioxide and chlorine gas.
3. Method as described above, characterized in that the enzymatic treatment step is carried out at a temperature between 10 and 90 degrees Celsius.
4. Method as described above wherein the temperature is between 40 and 80 degrees Celsius.
5. Method as described above wherein the temperature is between 60 and 80 degrees Celsius.
6. Method as described above, characterized in that the pH value of the pulp during the enzymatic treatment is from 7 up to and including 12.
7. Method as described above, characterized in that the pH value of the pulp during the enzymatic treatment is from 8 up to and including 11.
8. Method as described above, characterized in that the pH value of the pulp during the enzymatic treatment is from 9 up to and including 11.
9. Method as described above wherein the laccase is a bacterial laccase.
10. Method as described above wherein the laccase is obtainable from *Bacillus wakoensis*.
11. Method as described above wherein a laccase mediator is present before or during the enzymatic treatment.
12. Method as described above wherein the laccase mediator is syringaldehyde.
13. Method as described above wherein the pulp is wood pulp.
14. Method as described above wherein the pulp is mechanical pulp.
15. Method as described above wherein the pulp is chemical pulp.

EXAMPLES

Example 1: Preparation of Polypeptides According to SEQ ID NO:s 1-4

The DNA sequences according to SEQ ID NO:s 5-8, encoding the polypeptides according to SEQ ID NO:s 1-4 were commercially synthesized and cloned into a standard plasmid vector pET26a+ under the control of T7-RNA-polymerase promoter for expression in *Escherichia coli* BL21(DE3).

Protein production was carried out in *E. coli* BL21(DE3) strain according to the plasmid manufacturer protocol available at internet site richsingiser.com/4402/Novagen%20pET%20system%20manual.pdf. The incubation temperature for protein production was 30 degrees C., which was found optimal for maximum yield of the active protein. Cells were lysed using laccase lysis buffer (20 mM Sodium Citrate pH7.4, 1% Triton X100, 1 mM CuCl2) and heated at 60 degrees C. for 20 min. Coagulated cell debris was removed by centrifugation. The recombinant laccases were detected in the soluble fraction only, consistent with the notion that they are thermostable enzymes.

Example 2: Measuring Laccase Activity in Solution by DMP Oxidation

The term "laccase activity" is used herein to mean the capability to act as a laccase enzyme, which may be expressed as the maximal initial rate of the specific oxidation reaction. In some experiments relative activity was measured by oxidation of DMP (2,6-Dimethoxyphenol). Reaction course was monitored by change in absorbance at 468 nm (extinction coefficient of oxidized DMP at 468 nm is 14800 M-1 cm-1). The appropriate reaction time was determined to provide initial rates of oxidation when color development is linear in time. DMP concentration in the reaction mixture was 1 mM to provide maximum initial rates (substrate saturation conditions).

Typically, reactions were carried out in 200 ul in 96-well plates. 180 µl of enzyme dilution in Britton and Robinson buffer (0.04 M $H_3BO_3$, 0.04 M $H_3PO_4$ and 0.04 M $CH_3COOH$ that has been titrated to pH 8.0 with 0.2 M NaOH) was prepared in the assay plate and equilibrated to the desired temperature (70 degrees C.), then 20 uL of 10 mM DMP solution was added to start the reaction. The reaction was incubated at 70 degrees C. for 10-20 min. After that optical density at 468 nm was measured using microtiter plate reader. Sample containing no enzyme (only buffer and substrate) was used for background correction, OD reading from this sample was subtracted from all OD values.

One unit of laccase activity is defined as the enzyme amount oxidizing 1 micro mole of substrate per minute, one microkatal is the amount of enzyme oxidizing 1 micromol of substrate per second, and hence 10 millikatal equals 600,000 units. Absolute value of enzyme activity as measured in units or katals depends on the conditions under which this activity was determined and on the substrate used for activity measurement.

Example 3: Stability of Laccase Enzymes in Solution

Enzyme solutions at a concentration of 0.1 mg per ml in Britton and Robinson buffer were adjusted to pH 9.0 or 11.0 before pre-incubation. Pre-incubation was carried out at a temperature of 40 degrees Celsius or 70 degrees Celsius for 0 h, 1 h, 2 h, 3 h or 4 h.

After that, the residual activity was determined spectrophotometrically as described in Example 2. Initial activity (0 h) was taken as 100% for each enzyme (FIGS. 1A-1D).

Example 4: Pulp Delignification by Laccase

Pulp used in these experiments was high lignin spruce Kraft pulp (kappa number 56) collected after oxygen delignification stage before bleaching stage. The pulp was washed thoroughly with hot tap water prior to the experiments. The delignification process mediated by laccase was analyzed by measuring the consumption of dissolved oxygen in samples during laccase treatment and eventually by measuring of kappa number of the resulting pulp.

The dissolved oxygen measurements were made with a SensorLink PCM800 meter using a Clark oxygen electrode.

The reactions were run in a 1 L stirring reactor with automatic pH and temperature control at 0.5% pulp dry weight content at 40 and 70 degrees C. The pH in the reactor was adjusted with NaOH solution to pH 9 or pH 11 and maintained constant. The laccase was dosed at 1 ukat/g of the pulp dry weight as measured by DMP oxidation in solution at pH 8, 70 degrees C. with photometric detection as described in Example 2.

Prior to the reaction, the pulp suspension was equilibrated to the desired temperature and pH and air-saturated by stirring at 500 rpm in the reactor so that dissolved oxygen level was stable. This level was set as 100%. After that, the enzyme was added to the pulp and mixing continued for 1 min to distribute the enzyme and then stopped for 15 min. Substrate oxidation by the enzyme was followed by the gradual drop of dissolved oxygen as monitored by the oxygen probe. This oxygen drop is attributed to the fact that laccase is using oxygen as electron acceptor in the oxidation reaction and converts it to water, thus oxygen consumption can be directly linked to the enzymatic activity. The oxygen decrease remained essentially linear for at least 15 min. The slope value of oxygen decrease was taken as a measure of laccase enzyme activity (FIG. 2).

After 15 minutes of incubation, the mixing was resumed and oxygen levels stabilized again typically at a slightly lower level than 100% due to continuous oxygen consumption by the enzyme. After 45 min, stirring was stopped for 15 min again and residual laccase activity was measured again by following the oxygen depletion rate. The experiment was continued for 4 hours and 15 min in the same manner, stopping mixing in the beginning of every hour for 15 min, and finally at the end of the 4 hour incubation period. After the experiment, pulp was washed with 2% NaOH and subjected to Kappa number measurement.

Example 5: Measurement of Kappa Number

The Kappa number estimates the amount of chemicals required during bleaching of wood pulp to obtain a pulp with a given degree of whiteness. Since the amount of bleach needed is related to the lignin content of the pulp, the Kappa number can be used to monitor the effectiveness of the lignin-extraction phase of the pulping process. It is approximately proportional to the residual lignin content of the pulp.

The kappa number or lignin content can be calculated using the following formula: $K \approx c*l$, wherein K: Kappa number; c: constant$\approx$6.57 (dependent on process and wood); l: lignin content in percent.

The Kappa number for bleachable pulps are in the range of 25-30, sack paper pulps in the range 45-55 and pulps for corrugated fiberboard are in the range 60-90.

Kappa number was determined according to standard protocol Kappa Standard: ISO 302:2015 Pulps—Determination of kappa number; available at internet site: www.iso.org/iso/home/store/catalogue_ics/catalogue_detail_ics.-htm?csnumber=66 533.

Figure 5:
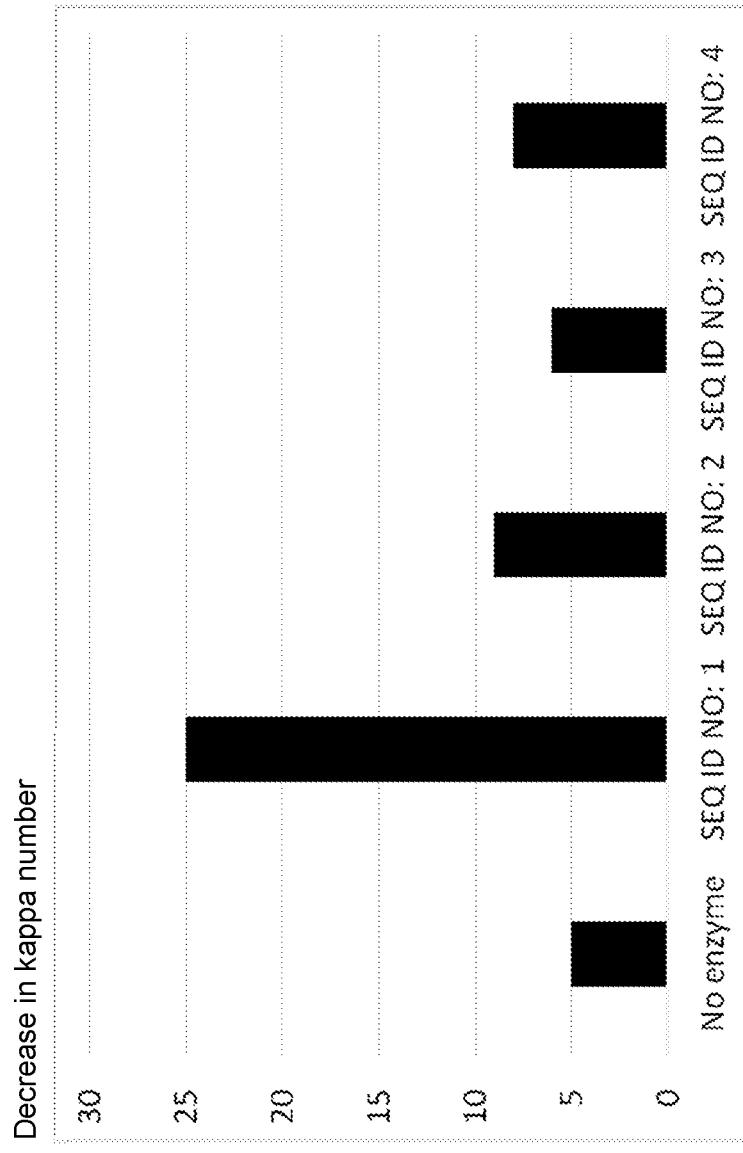

FIG. 5 shows the decrease in kappa numbers (indicative of the delignification of the pulp) after 4.25 hours of incubation as described in Example 4. Some decrease in Kappa number (increase in brightness) is caused by solubilisation of lignin in alkaline conditions at elevated temperature. This is why the control (without enzyme) shows a decrease in kappa number of 5. Oxidative degradation of lignin enhances the process of lignin solubilisation. That oxidative part can be followed by the oxygen consumption (FIG. 2).

Example 6: Lignin Depolymerization by Laccase

Lignin used in these experiments was Cat #471003 Sigma ALDRICH Lignin alkali low sulfonate content.

The lignin depolymerization process mediated by laccase was analyzed by measuring the consumption of dissolved oxygen in samples during laccase treatment (similar to example 4) and eventually by measuring of the molecular weight distribution of the lignin by size exclusion chromatography (SEC).

The dissolved oxygen measurements were made with a SensorLink PCM800 meter using a Clark oxygen electrode.

The reactions were run in a 1 L stirring reactor with automatic pH and temperature control at 2.2 gram per liter lignin at 40 or 70 degrees C. The pH in the reactor was adjusted with NaOH solution to pH 9 or 11 and maintained constant.

The laccase was dosed at 1 ukat/g of the lignin dry weight as measured by DMP oxidation in solution at pH 8 at 70 degrees C. with photometric detection as described in Example 2.

Prior to the reaction, the lignin solution or suspension was equilibrated to the desired temperature and pH and air-saturated by stirring at 500 rpm in the reactor so that dissolved oxygen level was stable. This oxygen level was set as 100%. A control experiment was performed without any enzyme. The enzyme was added to the lignin solution or suspension and mixing continued for 1 min to distribute the enzyme and then stopped for 15 min. Substrate oxidation by the enzyme was followed by the gradual drop of dissolved oxygen as monitored by the oxygen probe. The oxygen decrease remained essentially linear for at least 15 min. The slope value of oxygen decrease was taken as a measure of laccase enzyme activity (FIG. 2).

After 15 minutes of incubation, the mixing was resumed and oxygen levels stabilized again typically at a slightly lower level than 100% due to continuous oxygen consumption. After 45 min, stirring was stopped for 15 min again and residual laccase activity was measured again by following the oxygen depletion rate. The experiment was continued for 4 hours and 15 min in the same manner, stopping mixing in the beginning of every hour for 15 min, and finally at the end of the 4 hour incubation period. After the experiment, the solution or suspension was filtered with a 0.45 micrometer pore size filter and the flow-thrue was subjected to molecular weight distribution measurement by size exclusion chromatography (Example 7).

Example 7: Size Exclusion Chromatography

The molar mass measurements were performed with size exclusion chromatography using alkaline eluent (0.1M NaOH). For the molar mass measurements, the samples were diluted with 0.1M NaOH for the measurement consentration. In all cases the samples were filtered (0.45 μm) before the measurement.

The SEC measurements were performed in 0.1 M NaOH eluent (pH 13, 0.5 ml/min, T=25° C.) using PSS MCX 1000 & 100000 Ångstrom columns with a precolumn. The elution curves were detected using Waters 2998 Photodiode Array detector at 280 nm. The molar mass distributions (MMD) were calculated against polystyrene sulphonate (8×PSS, 3420-148500 g/mol) standards, using Waters Empower 3 software.

We found that in the control samples, the average molecular size was above 2000 Daltons for all temperatures and pH values. The enzyme according to SEQ ID NO: 1 was superior in depolymerizing lignin at all conditions tested (pH 9 or 11 and 40 and 70 degrees Celsius. The depolymerization was most effective at 70 degrees Celsius and pH 11. Under these conditions, over 70% of the lignin molecules obtained with the laccase according to SEQ ID NO: 1 were below 1000 Daltons after 4 hours of incubation, whereas the samples obtained with the enzymes according to SEQ ID NO: 2-4 were more comparable to the control samples.

The invention claimed is:

1. A method for lignin depolymerization, the method comprising:
   contacting a solution or suspension containing lignin with a laccase at alkaline pH,
   the laccase comprises an amino acid sequence at least 90% identical to SEQ ID NO: 1; and
   the lignin is depolymerized.

2. The method according to claim 1, wherein the solution or suspension containing lignin comprises a pulp.

3. The method according to claim 2, wherein the pulp is a mechanical pulp or a chemical pulp.

4. The method according to claim 2, further comprising bleaching the pulp.

5. The method according to claim 4, wherein bleaching the pulp comprises:
   the pulp with a bleaching chemical selected from the group consisting of peroxide, hydrogen peroxide, oxygen, ozone, chlorine dioxide and a mixture of chlorine dioxide and chlorine gas.

6. The method according to claim 1, wherein the solution or suspension containing lignin comprises at least 40% lignin as a fraction of the dry matter of the solution or suspension.

7. The method according to claim 1, wherein contacting the solution or suspension is carried out at a temperature between 10 and 90 degrees Celsius.

8. The method according to claim 7, wherein the temperature is above 40 degrees.

9. The method according to claim 7, wherein the temperature is below 50 degrees.

10. The method according to claim 1, wherein the pH of the solution or suspension is from 8 up to and including 12.

11. The method according to claim 10, wherein the pH is above 9.

12. The method according to claim 10, wherein the pH is below 12.

13. The method according to claim 1, wherein the laccase is produced in *E. coli*.

14. The method according to claim 13, wherein the laccase is a *Bacillus wakoensis* laccase.

15. The method according to claim 1, wherein the solution or suspension does not contain an electron mediator selected from the group consisting of 1-hydroxybenzotriazole (HBT), 2,2'-azino-bis-(3-ethylbenzothiazoline-6-sulfonic acid) (ABTS), acetosyringone, phenol, and violuric acid.

16. The method according to claim 2, wherein the pulp is wood pulp.

* * * * *